United States Patent [19]

Sakurai et al.

[11] Patent Number: 5,342,963
[45] Date of Patent: Aug. 30, 1994

[54] OPTICALLY ACTIVE PYRROLIDINE DERIVATIVE

[75] Inventors: Kuniya Sakurai; Kunisuke Izawa; Hiroyuki Izawa; Takashi Ineyama, all of Kawasaki; Tomihisa Ohta; Shigeo Nozoe, both of Sendai, all of Japan

[73] Assignee: Ajinomoto Co., Inc., Tokyo, Japan

[21] Appl. No.: 915,808

[22] PCT Filed: Nov. 26, 1991

[86] PCT No.: PCT/JP91/01619
§ 371 Date: Sep. 15, 1992
§ 102(e) Date: Sep. 15, 1992

[87] PCT Pub. No.: WO92/09605
PCT Pub. Date: Jun. 11, 1992

[30] Foreign Application Priority Data

Nov. 27, 1990 [JP] Japan ................. 2-324761
Nov. 28, 1990 [JP] Japan ................. 2-327681

[51] Int. Cl.$^5$ ................. C07D 207/00; C07D 405/00; C07D 401/00; C07D 487/00
[52] U.S. Cl. ................. 548/532; 548/517; 546/281; 540/302; 540/350
[58] Field of Search ................. 548/532, 517; 546/281

[56] References Cited

U.S. PATENT DOCUMENTS 4,876,383 10/1989 Nozoe .

FOREIGN PATENT DOCUMENTS 60-152461 8/1985 Japan .
60-208981 10/1985 Japan .
63-10758 1/1988 Japan .
1-175963 7/1989 Japan .

OTHER PUBLICATIONS

Tetrahedron Letters, vol. 29, No. 34, 1988, pp. 4305–4308, Tomihisa Ohta, et al., "Chirospecific Synthesis of (+)-PS-5 from L-Glutamic Acid".
Bulletin of the Chemical Society of Japan, vol. 60, No. 6, 1987, pp. 2091–2099, Azuma Watanabe, et al., "Total Synthesis of 6-Hydroxy-epi-PS 5 and 6-Methoxy-epi--PS 5".
Abstracts of the 29th Symposium on the Chemistry of Natural Products, 1987, pp. 87–93, K. Izawa.
CA 80(13):70632h, Della et al., 1973.
CA 114(19):1860642, Baxter et al., 1990.
March, Advanced Organic Chemistry, Wiley and Sons, N.Y., 1985, pp. 732–733.

*Primary Examiner*—Johann Richter
*Assistant Examiner*—Rebecca Cook
*Attorney, Agent, or Firm*—Oblon, Spivak, McClelland, Maier & Neustadt

[57] ABSTRACT

Optically active pyrrolidine derivative represented by the following formula (XI):

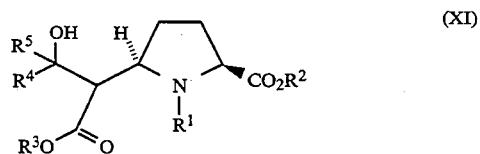

wherein $R^1$ represents a benzyl group $R^2$ represents an alkyl group having 1 to 6 carbon atoms, $R^3$ represents an alkyl group having 1 to 6 carbon atoms, a benzyl group or an allyl group, $R^4$ is selected from the group consisting of a hydrogen atom, an alkyl group having 1 to 6 carbon atoms which may be substituted with a protected hydroxyl group, a vinyl group, a phenyl group which may be substituted, a benzyl group which may be substituted, and a heterocyclic ring having 1 to 4 nitrogen or/and oxygen atoms, and $R^5$ represents a hydrogen atom or a methyl group.

This compound can be an intermediate for synthesis of carbapenem antibiotic compounds.

3 Claims, No Drawings

OPTICALLY ACTIVE PYRROLIDINE DERIVATIVE

DESCRIPTION

Technical Field

This invention is to provide novel carbapenam derivatives which are useful as preparation intermediates for synthesis of carbapenems which are now developing into various medicines such as β-lactam antibiotics having excellent antibacterial activities, a process for preparing the same, and also novel optically active pyrrolidine derivatives and a process for preparing the same.

Background Art

As for the novel carbapenam derivatives according to the present invention, various derivatives have been synthesized in order to strengthen antibacterial activities of carbapenem antibiotics or heightening the stability against an enzyme DHP-1 which deactivates carbapenems.

It is one of the means of synthesizing derivatives to introduce a hydroxyl group to the 6-position, but almost all the synthetic methods of carbapenems which have heretofore been developed relate to synthesis of 6-hydroxyethylcarbapenems. According to these methods, however, it is difficult to synthesize 6-hydroxy-6-hydroxyethylcarbapenems.

Among preparation methods of 6-hydroxycarbapenems which have heretofore been developed, there is a method where the 6-position of 6-ethylcarbapenems is hydroxylated (Bull. Chem. Soc. Jpn., 60, 2091 (1987)), but there is no method where a hydroxyl group is introduced to the 6-position of 6-hydroxyethyl-substituted carbapenems. Also, as a synthetic method of a 3-hydroxy-3-hydroxyethylazethidinone derivative which can be considered to be an intermediate for synthesis of such carbapenems, there has been known a method by T. Durst (Tetrahdedron Letters, 31, 3249 (1990)). However, this method involves many steps and also requires many further steps for converting it into a final carbapenem.

Under such a technical background, one of the objects of the present invention is to provide intermediates for synthesis of 6-hydroxy-6-hydroxyethylcarbapenems and a process for preparing the same.

Also, as for the novel optically active pyrrolidine derivatives according to the present invention, it is difficult to produce carbapenems by fermentation using bacteria due to their potent antibacterial activities so that it has been desired to develop a synthetic preparation process. As synthetic methods, there have been generally employed those ones where the optically active β-lactam portion is first synthesized and then the 5-membered ring is formed (T. Kametani et al., Heterocycles, 17, 463 (1982) and 25, 729 (1987)). As a more general method for synthesizing various kinds of substituted carbapenems as compared to these methods, the present inventors have developed a method in which L-pyrroglutamic acid derivatives are used as a starting material (S. Nozoe et al., Tetrahedron Letters, 29, 4305 (1988); Japanese Patent Application Laid-Open No. 72667/1988).

The main part of the above method using L-pyrroglutamic acid derivatives as a starting material can be shown by the following figure.

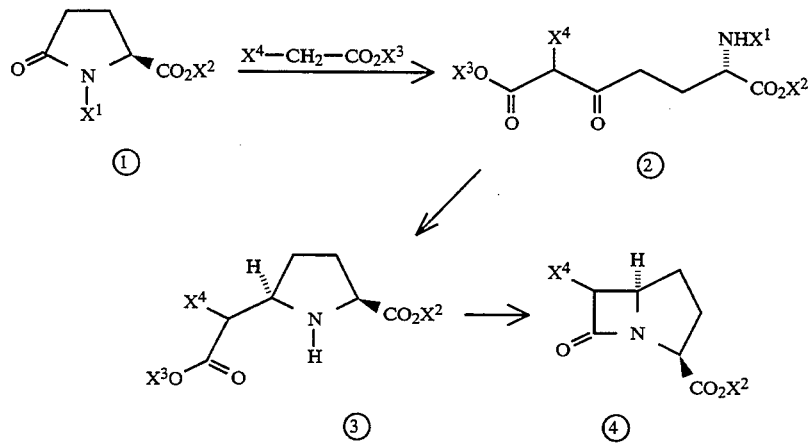

When $X^4$ is an alkyl group, a desired product can be obtained in a high yield by the said method, but when $X^4$ is a hydroxyalkyl group represented by the formula:

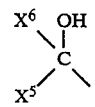

is to be synthesized, a reaction yield of the compound ② was not satisfactory for practical purposes.

In such a technical background, another object of the present invention is to develop a process for synthesizing, from an inexpensive L-pyrroglutamic acid derivative, 6-hydroxyalkylcarbapenems which are considered to be essential for developing potent antibacterial activities and a wide antibacterial spectrum, and for accomplishing the above, it is necessary to develop a process for synthesizing the compounds ③ and/or ④ in the above figure effectively.

DISCLOSURE OF THE INVENTION

First, the novel carbapenam derivatives of the present invention and a process for preparing the same is to be explained.

The present inventors have intensively studied in view of the above problems and, as a result, found that novel carbapenams represented by the following general formula (I) which are diols and can be useful intermediates for synthesis of 6-hydroxy-6-hydroxyethylcarbapenem can be easily produced by reacting a 6-ethylidenecarbapenam which can be easily obtained and represented by the following general formula (II) with osmium tetroxide, and accomplished the present invention based on these findings.

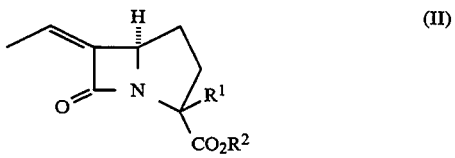

wherein R¹ represents a hydrogen atom or an organic group which can be eliminated under acidic or alkaline conditions, or reductively such as a methoxycarbonyl group or a benzyloxycarbonyl group, R² represents a hydrogen atom or a carboxyl-protective group such as a methyl group, and steric configuration at the 5-position represents the (R) configuration.

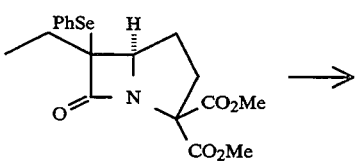

wherein R¹, R² and steric configuration at the 5-position are respectively the same as those of the formula (II).

Substrate ethylidenecarbapenams represented by the formula (II) can be easily prepared, for example, when R¹ represents a methoxycarbonyl group and R² represents a methyl group, by the oxidative elimination of the 6-phenylselenoether of the corresponding carbapenam.

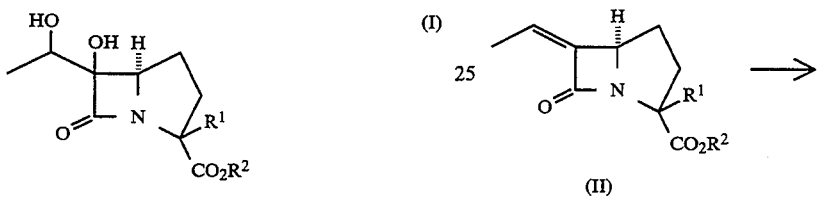

Also, when R¹ represents a hydrogen atom and R² represents a carboxyl-protective group, they can be produced by subjecting a corresponding 6-hydroxyethylcarbapenam to methanesulfonylation, followed by the action of a base such as DBU (1,8-diazabicyclo[5,4,0]-7-undecene).

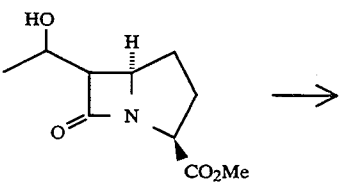

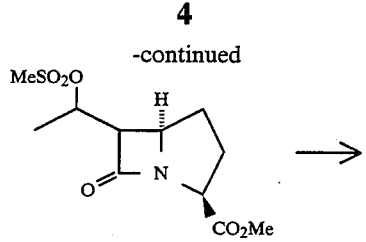

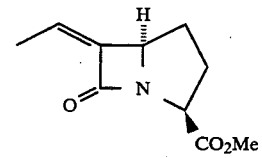

The reaction scheme in which a carbapenam derivative of the present invention represented by the general formula (I) is synthesized from a 6-ethylidenecarbapenam represented by the general formula (II) is shown below.

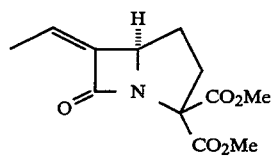

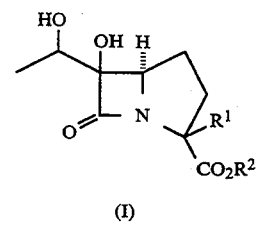

In the present reaction, the introduction of the two hydroxyl groups can be carried out by the action of osmium tetroxide on the 6-ethylidenecarbapenam (II). Also, it can be carried out by the action of osmium tetroxide together with a tertiary amine-N-oxide, suitably N-methylmorpholine-N-oxide. Osmium tetroxide may be used in an amount of 0.05 to 1 equivalent or so. In this reaction, when a cis (Z) ethylidenecarbapenam is used, the 6 (S) and 8 (S) isomer can be selectively obtained and, when a trans (E)-ethylidenecarbapenam is used, the 6(S) and 8 (R) isomer can be selectively obtained.

The present reaction can be carried out at 0° C. or so and at room temperature, and it is preferably carried out at 0° C. or so from the view points of stereoselectivity, etc.

As the reaction solvent, a solvent such as diethyl ether, benzene, pyridine, water, acetone, or a mixture of two or more thereof is used, and a 1:1 to 2 mixture of water and acetone is preferably used from the view points of solubility of the reactants, etc.

As for the reaction time, the reaction usually requires several hours to one day or so.

As for separation of a desired product from a reaction mixture, it can be easily carried out by a usual extraction operation followed by a usual purification operation such as chromatography using silica gel.

As for the process for producing the carbapenem skeleton from a novel carbapenam derivative represented by the general formula (I), for example, when $R^1$ represents a hydrogen atom and $R^2$ represents a carboxyl-protective group, the skeleton can be easily produced by using the method which was already reported by the present inventors (Abstracts of the 29th Symposium on the Chemistry of Natural Products, Japan, p. 87 (1987)). Also, when $R^1$ represents an alkoxycarbonyl group and $R^2$ represents a carboxyl-protective group, it can be produced by an already known method (Bull. Chem. Soc. Jpn., 60, 2091 (1987)).

Next, novel optically active pyrrolidine derivatives of the present invention and a process for producing the same are to be explained.

In order to solve the above problem, the present inventors have made an intensive study on an effective synthetic method of the compounds ③ and ④ in which $X^4$ is a hydroxyalkyl group or those compounds in which the group is suitably protected in the aforementioned figure, and as the result, they have found that optically active pyrrolidine derivatives which are novel compounds represented by the following general formula (XI) can be synthesized by reacting an optically active pyrrolidine derivative which is also a novel compound represented by the following general formula (XII) with a base and a carbonyl compound represented by the following general formula (XIII), and have also confirmed that a compound represented by the general formula (XI) can be converted into a carbapenem compound with good efficiency. The present invention has been made on these findings.

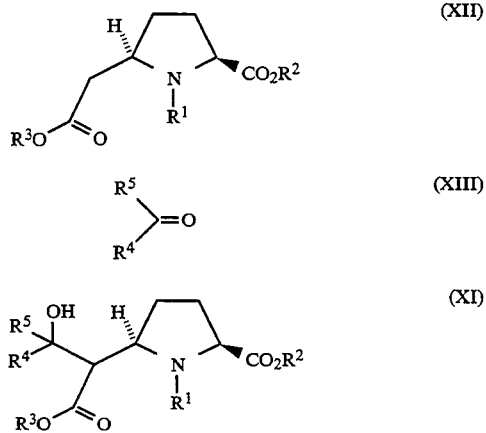

In the above formulae, $R^1$ represents a benzyl group, $R^2$ represents an alkyl group having 1 to 6 carbon atoms, $R^3$ represents an alkyl group having i to 6 carbon atoms, a benzyl group or an allyl group, $R^4$ represents either of a hydrogen atom, an alkyl group having 1 to 6 carbon atoms which may be substituted by a protected-hydroxyl group, a vinyl group, a phenyl group which may be substituted, a benzyl group which may be substituted, or a heterocyclic ring containing 1 to 4 nitrogen atom(s) or/and oxygen atom(s), and $R^5$ represents a hydrogen atom or a methyl group, respectively.

In the reaction from the formula (XII) to the formula (XI), it is one of the characteristic features of the present invention that a benzyl group is used as the N-protective group $R^1$. When other protective groups, for example, a benzyloxycarbonyl group, a t-butyloxycarbonyl group, etc., are used, there are provided various products. Only when a benzyl group is used, the reaction for producing a compound represented by the general formula (XI) can proceed without being accompanied by any side reaction and in a satisfactory yield thereof. Further, a benzyl group can be easily removed by catalytic hydrogenolysis.

Pyrrolidine derivatives (XII) which are compounds of the present invention and are also a starting material of the process of the present invention can be synthesized in a high yield by reacting a pyrrolidine derivative (which corresponds to the compound of the formula (XII) in which $R^1$ is a hydrogen atom) obtained from an L-pyroglutamic acid derivative according to the methods described in Japanese Patent Application Laid-Open No. 72667/1988 and Tetrahedron Letters, 29, 4305 (1988), with benzyl chloride or benzyl bromide at a temperature of 0° to 50° C. in an organic solvent such as dichloromethane, chloroform, tetrahydrofuran, etc., in the presence of a base such as triethylamine, potassium carbonate, etc.

An optically active pyrrolidine derivative (XI) can be synthesized by treating an optically active pyrrolidine derivative (XII) with a base followed by reacting a carbonyl compound (XIII).

As the base, there may be used lithium diisopropylamide, lithium hexamethyldisilazide, potassium hexamethyldisilazide, potassium t-butoxide, etc.

As the reaction solvent, there may be used an ether solvent such as tetrahydrofuran, ethyl ether, etc., a hydrocarbon solvent such as toluene, etc., an aprotic polar solvent such as N,N-dimethylformamide, etc., or a mixture of two or more thereof.

Also, there may be, though not essential, added hexamethylphosphoric triamide, N,N'-dimethylpropylene urea, N,N,N',N'-tetramethylethylenediamine, etc. as a reaction aid. By using such a reaction aid, a merit of stabilizing anions, etc. can be obtained.

The reaction temperature is generally from $-80°$ C. or so to room temperature, preferably $-20°$ to $-70°$ C. from the view point of industrial utilization.

A carbonyl compound (XIII) is desirably used in at least 1 equivalent to a compound (XII), and it is added to the reaction solution, preferably as a solution of the above reaction solvent.

After completion of the reaction, purification can be carried out by usual methods, such as extraction, washing, recrystallization and chromatography.

The optically active pyrrolidine derivatives (XI) can be led to compounds having potent antibacterial activities such as carbapenems having a hydroxyalkyl group at the 6-position including, for example, thienamycin, carpetimycin derivatives, etc. by the method as shown in Reference examples. Accordingly, the optically active pyrrolidine derivatives of the present invention represented by the general formulae (XI) and (XII) are useful as intermediates for the synthesis of carbapenems.

BEST MODE FOR CARRYING OUT THE INVENTION

The present invention will be further explained by the following Examples.

EXAMPLE 1

(1) [structure: ethylidenecarbapenam with CO2Me, CO2Me]

→

(2) [structure: diol with HO, OH, H, CO2Me, CO2Me]

82 mg (0.324 mmol) of the ethylidenecarbapenam (1) was dissolved in a mixed solvent of 4 ml of acetone and 2 ml of water. To the solution were added 150 mg (1.28 mmol) of N-methylmorpholine N-oxide and 0.4 ml (0.066 mmol) of aqueous 0.164M osmium tetroxide solution, and the mixture was stirred at 0° C. overnight. An aqueous 10% $Na_2SO_3$ solution was added to the reaction mixture and the mixture was stirred at room temperature for further one hour. Thereafter, the reaction mixture was saturated with sodium chloride and extracted with dichloromethane. After drying over $MgSO_4$, the solvent was removed by distillation. The residue was purified by a preparative TLC (ethyl acetate) to obtain the diol (2). 53.7 mg (57.7%).

NMR ($CDCl_3$, ppm): 1.20 (3H, d), 1.65 (2H, br), 1.85–2.10 (2H, m), 2.65 (2H, m), 3.82 (6H, s), 3.95 (1H, t), 4.38 (1H, q).

EXAMPLE 2

(3) [structure]

→

(4) [structure]

In the same manner as in Example 1, 16 mg (21.7%) of the diol (4) was obtained from 65 mg of the ethylidenecarbapenam (3).

NMR ($CDCl_3$, ppm): 1.38 (3H, d, J=6.6 Hz), 1.80 (2H, br), 2.20 (2H, m), 2.65 (2H, m), 3.80 (3H, s), 3.82 (3H, s), 3.90 (1H, m), 4.20 (1H, br).

EXAMPLE 3

(5) [structure]

→

(6) [structure]

In the same manner as in Example 1, 8 mg (17%) of the diol (6) was obtained from 40 mg of the ethylidenecarbapenam (5).

NMR ($CDCl_3$, ppm): 1.30 (3H, d, J=6.6 Hz), 1.95 (6H, m), 3.59 (1H, J=6.9 Hz, 8.4 Hz), 3.73 (3H, s), 3.84 (1H, dd, J=5.1 Hz, 9 Hz), 4.26 (1H, q, J=6.6 Hz).

IR ($CHCl_3$, cm$^{-1}$): 1781, 1737, 1216.

EXAMPLE 4

(7) [structure]

→

(8) [structure]

In the same manner as in Example 1, 8 mg (11.5%) of the diol (8) was obtained from 59 mg of the ethylidenecarbapenam (7).

NMR ($CDCl_3$, ppm): 1.31 (3H, d, J=6.6 Hz), 1.6 (2H, br), 1.5–2.1 (4H, m), 3.51 (1H, t, J=7.5 Hz), 3.71 (3H, s), 3.79 (1H, t, J=6.9 Hz), 4.13 (1H, q, J=6.6 Hz).

In the following Examples, the following abbreviations are used.
Me: methyl
$^i$Pr: isopropyl
Bn: benzyl
$^t$Bu: t-butyl
Z: benzyloxycarbonyl
THF: tetrahydrofuran
NMR: nuclear magnetic resonance spectrum (proton)
IR: infrared absorption spectrum Also, the proton NMR spectra (300 MHz) is shown by (ppm) values using chloroform-d as the solvent and tetramethyl silane as the internal standard unless otherwise specifically mentioned, and coupling constants (J) are shown by Hz.

EXAMPLE 5

Synthesis of Isopropyl (2S,5R)-1-Benzyl-5-[2-Hydroxy-2-Methyl-1-(t-Butoxycarbonyl)Propyl]Pyrrolidine-2-Carboxylate (Compound 2)

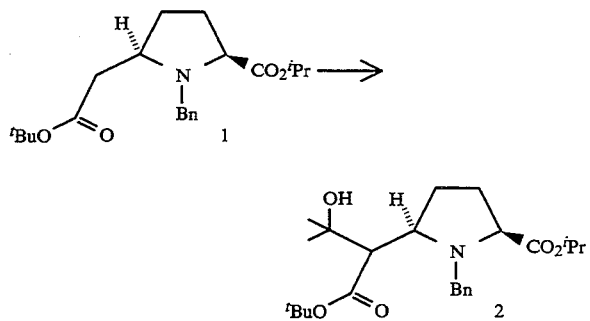

Under an argon atmosphere, n-butyl lithium (1.56 M/hexane, 4.2 ml, 6.6 mmol) was added dropwise to a THF (28 ml) solution of diisopropylamine (1.0 ml, 7.1 mmol) at −45° C., and the mixture was stirred under ice-cooling for 12 minutes. To the solution was added dropwise a THF (4 ml) solution of isopropyl (2S,5R)-1-benzyl-5-(t-butoxycarbonyl)pyrrolidine-2-carboxylate (Compound 1, 2.16 g, 5.98 mmol) at −70° C. and the mixture was stirred for 30 minutes. Then, a THF (1 ml) solution of acetone (0.60 ml, 8.2 mmol) was added dropwise and the mixture was stirred for one hour.

The reaction was stopped by adding 40 ml of aqueous 20% ammonium chloride solution. The reaction mixture was extracted with ethyl acetate, and the ethyl acetate solution was washed with an aqueous NaCl-saturated solution and dried over anhydrous sodium sulfate. The solvent was removed by distillation under reduced pressure. The residue was divided into two portion, and each portion was subjected to a medium pressure silica gel column chromatography (Lobar size B, ethyl acetate-hexane 1:6) to recover the unreacted starting material (Compound 1, 711 mg, 33%) as well as to obtain a mixture of the two isomers of Compound 2 (Compounds 2a and 2b (29:71), colorless viscous liquid, 1.31 g, 52%).

Spectrum data of isopropyl (2S,5R)-1-benzyl-5-[(R)-2-hydroxy-2-methyl-1-(t-butoxycarbonyl)propyl]pyrrolidine-2-carboxylate (Compound 2a);

IR (neat): 1720 cm$^{-1}$.

NMR: 1.01 (3H, d, J=6.3), 1.05 (3H, d, J=6.2), 1.26 (3H, s), 1.44 (3H, s), 1.47 (9H, s), 1.6–1.75 (1H, m, 4-CH), 1.90–2.06 (2H, m, 4-CH and 3-CH), 2.07–2.22 (1H, m, 3-CH), 2.61 (1H, d, J=10.6, 6-CH), 3.41 (1H, t, J=8.2, 2-CH), 3.67 (1H, d, J=12.6), 3.64–3.73 (1H, m, 5-CH), 4.22 (1H, d, J=12.6), 4.75 (1H, sept, J=6.3), 6.73 (1H, s, OH), 7.2–7.4 (5H, m).

Spectrum data of isopropyl (2S,5R)-1-benzyl-5-[(S)-2-hydroxy-2-methyl-1-(t-butoxycarbonyl)propyl]pyrrolidine-2-carboxylate (Compound 2b);

IR (neat): 1735, 1720 cm$^{-1}$.

NMR: 1.12 (3H, d, J=6.3), 1.13 (3H, d, J=6.3), 1.26 (3H, s), 1.41 (3H, s), 1.49 (9H, s), 1.79–1.91 (1H, m, 4CH), 1.92–2.01 (2H, m, 3-CH$_2$), 2.13 (1H, m, 4-CH), 2.79 (1H, d, J=5.9, 6-CH$_2$), 3.37 (1H, t, J=7.2, 2-CH), 3.50 (1H, dt, J=7.8, 6, 5-CH), 3.67 (1H, d, J=13.6), 4.08 (1H, d, J=13.6), 4.84 (1H, sept, J=6.3), 5.40 (1H, s, OH), 7.2–7.35 (5H, m). (Compound 4)

EXAMPLE 6

SYNTHESIS OF METHYL (2-5R)-1-BENZYL-5-[2-HYDROXY-2-METHYL-1-(t-BUTOXYCARBONYL)PROPYL]PYRROLIDINE-2-CARBOXYLATE (Compound 4)

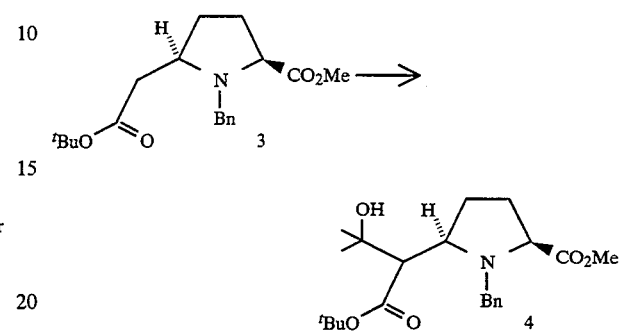

In the same manner as in Example 11, methyl (2S,5R)-1-benzyl-5-(t-butoxycarbonyl) pyrrolidine-2-carboxylate (Compound 3, 199 rag, 0.60 mmol) was reacted with acetone (0.058 ml, 0.79 mmol).

The reaction mixture was purified by a medium pressure silica gel column chromatography (Lobar size B, ethyl acetate-hexane 1:5) to recover the unreacted starting material (Compound 3, 115 mg, 58%) as well as to obtain a mixture of the two isomers of Compound 4 (Compound 4a, colorless viscous material, 10 mg, 5% and Compound 4b, colorless viscous material, 40 mg, 17%).

Spectrum data of methyl (2S,5R)-1-benzyl-5-[(R)-2-hydroxy-2-methyl-1-(t-butoxycarbonyl)propyl]pyrrolidine-2-carboxylate (Compound 4a);

NMR: 1.25 (3H, s), 1.42 (3H, s), 1.47 (9H, s), 1.65–1.75 (1H, m, 4-CH), 1.89–2.20 (3H, m, 3-CH$_2$ and 4-CH), 2.59 (1H, d, J=10.0, 6-CH), 3.42 (3H, s), 3.45 (1H, t, J=7.5, 2CH), 3.61–3.7 (1H, m, 5-CH), 3.68 (1H, d, J=12.8), 4.22 (1H, d, J=12.8), 7.2–7.4 (5H, m).

Spectrum data of methyl (2S,5R)-1-benzyl-5-[(S)-2-hydroxy-2-methyl-1-(t-butoxycarbonyl)propyl]pyrrolidine-2-carboxylate (Compound 4b);

NMR: 1.24 (3H, s), 1.38 (3H, s), 1.50 (9H, s), 1.79–2.11 (4H, m, 3-CH$_2$ and 4-CH$_2$), 2.69 (1H, d, J=6.1, 6-CH), 3.41 (1H, t, J=7.3, 2-CH), 3.50 (3H, s), 3.55 (1H, m, 5CH), 3.68 (1H, d, J=13.7), 4.07 (1H, d, J=13.7), 5.29 (1H, s, OH), 7.2–7.35 (5H, m).

EXAMPLE 7

SYNTHESIS OF ISOPROPYL (2S,5R)-1-BENZYL-5-[2-HYDROXY-2-METHYL-1-(METHOXYCARBONYL)PROPYL]PYRROLIDINE-2-CARBOXYLATE (Compound 6)

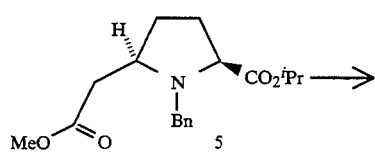

-continued

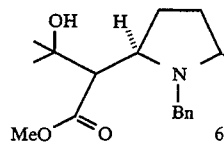

In the same manner as in Example 11, isopropyl (2S,5R)-1-benzyl-5-(methoxycarbonyl) pyrrolidine-2-carboxylate (Compound 5, 208 mg, 0.65 mmol) was reacted with acetone (0. 062 ml, 0.84 mmol). The reaction mixture was purified by a medium pressure silica gel column chromatography (Lobar size B, ethyl acetate-hexane 1:5) to recover the unreacted starting material (Compound 5, 100 mg, 48%) as well as to obtain a mixture of the two isomers of Compound 6 (Compound 6a, colorless viscous material, 15 mg, 6% and Compound 6b, colorless viscous material, 99 mg, 40%). Spectrum data of isopropyl (2S,5R)-1-benzyl-5-[(R)-2-hydroxy-2 -methyl-1-(methoxycarbonyl)propyl]pyrrolidine-2-carboxylate (Compound 6a);

NMR: 1.01 (3H, d, J=6.3), 1.06 (3H, d, J=6.2), 1.22 (3H, s), 1.44 (3H, s), 1.57-1.68 (1H, m, 4-CH), 1.89-2.06 (2H, m, 3-CH and 4-CH), 2.10-2.21 (1H, m, 3-CH), 2.76 (1H, d, J=10.3, 6-CH), 3.41 (1H, t, J=8.1, 2-CH), 3.66 (1H, d, J=12.5), 3.70 (3H, s), 3.65-3.76 (1H, m, 5-CH), 4.23 (1H, d, J=12.5), 4.75 (1H, sept, J=6.3), 6.62 (1H, s, OH), 7.2-7.4 (5H, m).

Spectrum data of isopropyl (2S,5R)-1-benzyl-5-[(S)-2-hydroxy-2-methyl-1-(methoxycarbonyl)propyl]pyrrolidine-2-carboxylate (Compound 6b);

NMR: 1.06 (3H, d, J=6.2), 1.10 (3H, d, J=6.3), 1.23 (3H, s), 1.32 (3H, s), 1.89-2.08 (4H, m, 3-CH₂ and 4-CH₂), 2.76 (1H, d, J=7.1, 6-CH), 3.32 (1H, m, 2-CH), 353-3.63 (1H, m, 5-CH), 3.60 (1H, d, J=13.4), 3.75 (3H, s), 4.09 (1H, d, J=13.4), 4.49 (1H, s, OH), 4.77 (1H, sept, J=6.3), 7.2-7.35 (5H, m).

EXAMPLE 8

In the same manner as in Example 11, Compound 1 (202 mg, 0.56 mmol) was reacted, except that toluene was used as the reaction solvent.

The unreacted starting material was recovered in a 80 recovery rate, and Compound 2 was obtained in a 15% yield (Compounds 2a and 2b, 1:3).

EXAMPLE 9

In the same manner as in Example 11, Compound 1 (210 mg, 0.58 mmol) was reacted, except that prior to adding Compound 1 to a lithium diisopropylamide solution, N,N,N',N'-tetramethylethylenediamine (0.105 ml, 0.70 mmol) was added.

The unreacted starting material was recovered in a 50 recovery rate, and Compound 2 was obtained in a 45% yield (Compounds 2a and 2b, 1:3).

EXAMPLE 10

Synthesis of Methyl (2S,5R)-1-Benzyl-5-[2-Hydroxy-1-(t-Butoxycarbonyl)-Propyl]Pyrrolidine-2-Carboxylate (Compound 7)

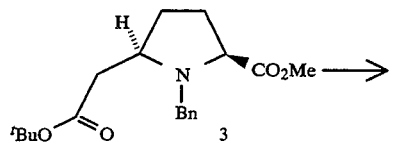

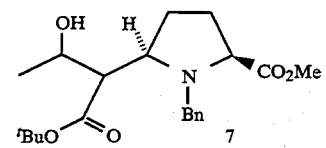

Under an argon atmosphere, n-butyl lithium (1.68M/hexane, 7.9 ml, 13.3 mmol) was added dropwise to a THF (100 ml) solution of diisopropylamine (2.0 ml, 14 mmol) at −70° C., and the mixture was stirred for 35 minutes. To the solution was added dropwise a THF (20 ml) solution of Compound 3 (4.00 g, 12.0 mmol) at −70° C. and the mixture was stirred for 20 minutes. Then, a THF (15 ml) solution of acetaldehyde (about 2 ml, 40 mmol) was added dropwise and the mixture was stirred for 1.5 hours.

The reaction was stopped by adding 16 ml of water. The reaction mixture was extracted with ethyl acetate, and the ethyl acetate solution was washed with an aqueous NaCl-saturated solution and dried over anhydrous sodium sulfate. The solvent was removed by distillation under reduced pressure. The residue was purified by a medium pressure silica gel column chromatography (Lobar size C, ethyl acetate-hexane 1 : 4) to recover the unreacted starting material (Compound 3, 1.41 g, 42%) as well as to obtain a mixture of two isomers of Compound 7 (Compounds 7a and 7b (2:1), colorless viscous liquid, 1.91 g, 42%).

Spectrum data of methyl (2S,5R)-1-benzyl-5-[(1R,2R)-2-hydroxy-1-(t-butoxycarbonyl)propyl]pyrrolidine-2-carboxylate (Compound 7a);

Mass spectrum m/z=377 (M+).

IR (neat): 3506, 1729 cm⁻¹.

NMR: 1.29 (3H, d, J=6.6), 1.49 (9H, s), 1.70-2.10 (4H, m, 3-CH₂ and 4-CH₂), 2.55 (1H, dd J=8.8 3.6 6-CH), 3.38-3.45 (1H, m, 2-CH), 3.44 (3H, s), 3.51 (1H, m, 5-CH), 3.75 (1H, d, J=13.4), 3.90-4.0 (1H, br-d, OH), 4.22 (1H, d, J=13.4), 4.28 (1H, m, 8-CH), 7.2-7.4 (5H, m).

Spectrum data of methyl (2S,5R)-1-benzyl-5-[(1S, 2S)-2-hydroxy-1-(t-butoxycarbonyl)propyl]pyrrolidine-2-carboxylate (Compound 7b);

NMR (part): 1.24 (3H, d, J=6.6), 1.46 (9H, s), 2.46 (1H, dd, J=7.6, 3.0, 6-CH), 3.51 (3H, s), 3.70 (1H, d, J=14.0), 3.94 (1H, d, J=14.0), 4.10 (1H, br, 8-CH).

EXAMPLE 11

In the same manner as in Example 16, Compound 3 (690 mg, 2.07 mmol) was reacted with a large excess of acetaldehyde. The unreacted starting material (Compound 3, 206 mg, 30%) was recovered and also a mixture of two isomers of Compound 7 (Compounds 7a and 7b (4:1), 340 mg, 43.5%) and a third isomer (Compound 7c, 75 mg, 10%) were obtained.

Spectrum data of Compound 7c;
NMR: 1.24 (3H, d, J=6.0), 1.45 ( 9H, s), 1.82–2.14 (3H, m, 3-CH$_2$ and 4-CH), 2.18–2.30 (1H, m, 4-CH), 2.70 (1H, dd, J=10.0, 2.8, 6-CH), 3.28 (1H, m, 5-CH), 3.39 (1H, dd, J=8.5, 6.6, 2-CH), 3.44 (3H, s), 3.59 (1H, d, J=13.0), 4.10 (1H, d, J=13.0), 4.32 (1H, m, 8-CH), 6.51 (1H, s, OH), 7.2–7.4 (SH, m).

EXAMPLE 12

In the same manner as in Example 16, Compound 3 (100 mg, 0.30 mmol) was reacted, except that prior to adding Compound 3 to a lithium diisopropylamide solution, hexamethylphosphorictriamide (0.06 ml) was added.

A mixture of the two isomers of Compound 7 (Compounds 7a and 7b (3:1), 20 mg, 18%) was obtained.

EXAMPLE 13

In the same manner as in Example 16, Compound 3 (2.00 g, 6.00 mmol) was reacted, except that prior to adding acetaldehyde, diethylzinc (6.0 mmol) was added and the mixture was stirred for 30 minutes.

A mixture of the two isomers of Compound 7 (Compounds 7a and 7b (3:1), 707 mg, 31%) was obtained.

EXAMPLE 14

The procedure was the same as in Example 16, except that lithium hexamethyldisilazide was used as the base. That is, under an argon atmosphere, n-butyl lithium (1.56M/hexane, 2.1 ml, 3.3 mmol) was added dropwise to a THF (25 ml) solution of hexamethyldisilazane (0.76 ml, 3.6 mmol) at −70° C., and the mixture was stirred for 35 minutes. To the solution was added dropwise a THF (7 ml) solution of Compound 3 (1.00 g, 3.0 mmol) at −70° C., and the mixture was stirred for one hour. Subsequently, a THF (5 ml) solution of acetaldehyde (about 0.7 ml, 13 mmol) was added dropwise and the mixture was stirred for 2 hours.

The reaction was stopped by adding 15 ml of water. The reaction mixture was extracted with ethyl acetate, and the ethyl acetate solution was washed with an aqueous NaCl-saturated solution and dried over anhydrous sodium sulfate. The solvent was removed by distillation under reduced pressure. The residue was purified by a medium pressure silica gel column chromatography (Lobar size B, ethyl acetate-hexane 1:5) to recover the unreacted starting material (Compound 3, 657 mg, 66%) as well as to obtain a mixture of the two isomers of Compound 7 (Compounds 7a and 7b (1:1), 110 mg, 10%).

EXAMPLE 15

The procedure was the same as in Example 16, except that potassium hexamethyldisilazide was used as the base. That is, under an argon atmosphere, to a THF (2 ml) solution of potassium hexamethyldisilazide (0.5 M/toluene, 0.72 ml, 0.36 mmol) was added dropwise a THF (1.5 ml) solution of Compound 3 (100 mg, 0.30 mmol) at −70° C., and the mixture was stirred for 50 minutes. Subsequently, a THF (1.5 ml) solution of acetaldehyde (about 0.1 ml, 2 mmol) was added dropwise thereto and the mixture was stirred for 2.5 hours.

The reaction was stopped by adding 12 ml of water. The reaction mixture was extracted with ethyl acetate, and the ethyl acetate solution was washed with an aqueous NaCl-saturated solution and dried over anhydrous sodium sulfate. The solvent was removed by distillation under reduced pressure. The residue was purified by a medium pressure silica gel column chromatography (Lobar size A, ethyl acetate-hexane 1:5) to recover the unreacted starting material (Compound 3, 62 g, 62%) as well as to obtain a mixture of the two isomers of Compound 7 (Compounds 7a and 7b (9:10), 19 mg, 17%).

EXAMPLE 16

Synthesis of Isopropyl (2S,5R)-1-Benzyl-5-[2-Hydroxy-1-(t-Butoxycarbonyl)-Propyl]Pyrrolidine-2-Carboxylate (Compound 8)

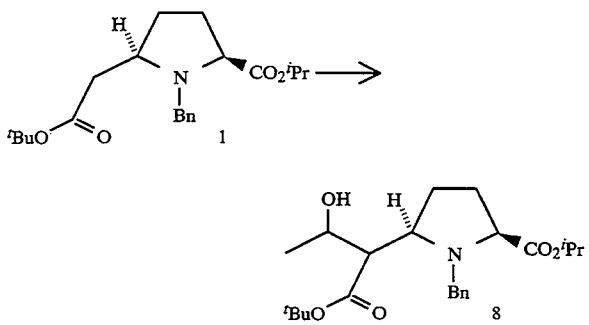

Under an argon atmosphere, n-butyl lithium (1.6M/hexane, 11.5 ml, 18.4 mmol) was added dropwise to a THF (70 ml) solution of diisopropylamine (2.8 ml, 20 mmol) at −70° C., and the mixture was stirred for 30 minutes. To the solution was added dropwise a THF (15 ml) solution of Compound 1 (6.03 g, 16.7 mmol), and the mixture was stirred for 50 minutes. Subsequently, a THF (7 ml) solution of acetaldehyde (2 ml, 36 mmol) was added dropwise thereto, and the mixture was stirred for one hour.

The reaction was stopped by adding 10 ml of an aqueous 20% ammonium chloride solution. The reaction mixture was extracted with ethyl acetate, and the ethyl acetate solution was washed with an aqueous NaCl-saturated solution and dried over anhydrous sodium sulfate. The solvent was removed by distillation under reduced pressure. The residue was purified by a medium pressure silica gel column chromatography (Lobar size C, ethyl acetate-hexane 1:4, divided into two) to obtain an isomer of Compound 8 (Compound 8a, colorless viscous liquid, 0.40 g, 6%) and a mixture of the three isomers (Compounds 8a, 8b and 8c (24:59:17), pale yellow viscous liquid, 5.70 g, 84%).

Spectrum data of isopropyl (2S,5R)-1-benzyl-5-[(1R, 2R)-2-hydroxy-1-(t-butoxycarbonyl)propyl]pyrrolidine-2-carboxylate (Compound 8a);
IR (neat): 3423, 1727 cm$^{-1}$.
NMR: 1.05 (3H, d, J=6.3), 1.10 (3H, d, J=6.3), 1.29 (3H, d, J=6.6, 9-CH$_3$), 1.49 (9H, s), 1.68–1.80 (1H, m, 4-CH), 1.84–1.99 (2H, m, 3-CH and 4-CH), 2.00–2.11 (1H, m, 3-CH), 2.55 (1H, dd, J=9.0, 3.3, 6-CH), 3.39 (1H, t, J=7.5, 2-CH), 3.55 (1H, ddd, J=9.0, 7.1, 4.1, 5-CH), 3.76 (1H, d, J=13.5), 4.04 (1H, br, OH), 4.22 (1H, d, J=13.5), 4.30 (1H, br, 8-CH), 4.79 (1H, sept, J=6.3), 7.2–7.35 (5H, m).

Spectrum data of isopropyl (2S,5R)-1-benzyl-5-[(1S, 2R)-2-hydroxy-1-(t-butoxycarbonyl)propyl]pyrrolidine-2-carboxylate (Compound 8b);
IR (neat): 3342, 1727 cm$^{-1}$.
NMR: 1.07 (3H, d, J=6.6), 1.10 (3H, d, J=6.3), 1.24 (3H, d, J=6.0, 9-CH$_3$), 1.45 (9H, s), 1.80–2.11 (3H, m, 3-CH$_2$ and 4-CH), 2.15–2.29 (1H, m, 4-CH), 2.69 (1H, dd, J=10.0, 3.0, 6-CH), 3.27 (1H, ddd, J=8.4, 6.9, 3.0, 5-CH), 3.36 (1H, dd, J=8.9, 5.6, 2-CH), 3.60 (1H, d, J=13.2), 4.08 (1H, d, J=13.2), 4.13 (1H, dq, J=10.0, 6.0, 8-CH), 4.79 (1H, sept, J=6.3), 6.36 (1H, s, OH), 7.2–7.4 (5H, m).

Spectrum data of isopropyl (2S,5R)-1-benzyl-5-[(1S, 2S)-2-hydroxy-1-(t-butoxycarbonyl)propyl]pyrrolidine-2-carboxylate (Compound 8c);

NMR (part): 1.10 (3H, d, J=6), 1.16 (3H, d, J=6.3), 1.25 (3H, d, J=6, 9-CH₃), 1.45 (9H, s), 2.48 (1H, dd, J=7.7, 3.2, 6-CH), 3.46 (1H, m, 5-CH), 3.70 (1H, d, J=14.1), 3.92 (1H, d, J=14.1), 4.10 (1H, br, 8-CH), 4.86 (1H, sept, J=6.3), 7.2–7.4 (5H, m).

EXAMPLE 17

Synthesis of Isopropyl (2S,5R)-1-Benzyl-5-[2-Hydroxy-1-(T-Butoxycarbonyl)-Butyl]Pyrrolidine-2-Carboxylate (Compound 9)

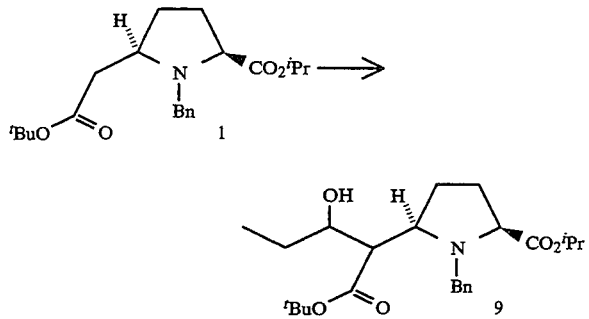

In the same manner as in Example 11, Compound 1 (365 mg, 1.01 mmol) was reacted with propionaldehyde (0.10 ml, 1.4 mmol).

The reaction mixture was purified by a medium pressure silica gel column chromatography (Lobar size B, ethyl acetate-hexane 1:6) to recover the unreacted starting material (Compound 1, 93 mg, 26%) as well as to obtain an isomer of Compound 9 (Compound 9a, colorless viscous material, 52 mg, 12%) and a mixture of the two other isomers (Compounds 9b and 9c (79:21), colorless viscous material, 211 mg, 50%).

Spectrum data of isopropyl (2S,5R)-1-benzyl-5-[(1R, 2R)-2-hydroxy-1-(t-butoxycarbonyl)butyl]pyrrolidine-2-carboxylate (Compound 9a);

Mass spectrum m/z=419 (M+).

IR (neat): 3417, 1727 cm⁻¹.

NMR: 1.02 (3H, d, J=7.4), 1.06 (3H, d, J=6.0), 1.11 (3H, d, J=6.3), 1.48 (9H, s), 1.45–1.6 (2H, m, 9-CH₂), 1.68–1.81 (1H, m, 4-CH), 1.82–2.10 (3-CH₂ and 4-CH), 2.57 (1H, d, J=9.0, 3.0, 6CH), 3.39 (1H, t, J=7.2, 2-CH), 3.54 (1H, ddd, J=9.0, 7.0, 4.4, 5-CH), 3.49–3.64 (1H, br, OH), 3.78 (1H, d, J=13.5), 3.97 (1H, br, 8-CH), 4.22 (1H, d, J=13.5), 4.80 (1H, sept, J=6.3), 7.2–7.35 (5H, m).

Spectrum data of isopropyl (2S,5R)-1-benzyl-5-[(1S, 2R)-2-hydroxy-1-(t-butoxycarbonyl)butyl]pyrrolidine-2-carboxylate (Compound 9b);

NMR: 1.02 (3H, d, J=7.5), 1.08 (3H, d, J=6.3), 1.12 (3H, d, J=6.3), 1.44 (9H, s), 1.4–1.65 (2H, m, 9-CH₂), 1.80–2.10 (3H, m, 3-CH₂ and 4-CH), 2.23 (1H, 4-CH), 2.76 (1H, dd, J=10.2, 3.0, 6-CH), 3.25 (1H, ddd, J=8.6, 7.4, 3.0, 5-CH), 3.55 (1H, dd, J=8.7, 5.5, 2-CH), 3.63 (1H, d, J=13.2), 4.05 (1H, d, J=13.2), 4.12 (1H, ddd, J=10.2, 7.5, 2.7, 8-CH), 4.82 (1H, sept, J=6.3), 6.26 (1H, br, OH), 7.2–7.35 (5H, m).

Spectrum data of isopropyl (2S,5R)-1-benzyl-5-[(1S, S)-2-hydroxy-1-(t-butoxycarbonyl)butyl]pyrrolidine-2-carboxylate (Compound 9c);

NMR (part): 0.98 (3H, d, J=7.5), 1.11 (3H, d, J=6.3), 1.17 (3H, d, J=6.3), 1.43 (9H, s), 2.55 (1H, dd, J=7.8, 2.7, 6-CH), 3.69 (1H, d, J=14.0), 3.93 (1H, d, J=14.0), 4.86 (1H, sept, J=6.3).

EXAMPLE 18

Synthesis of Isopropyl (2S,5R)-1-Benzyl-5-[2-Hydroxy-2-Phenyl-1-(T-Butoxycarbonyl)Ethyl]Pyrrolidine-2-Carboxylate (Compound 10)

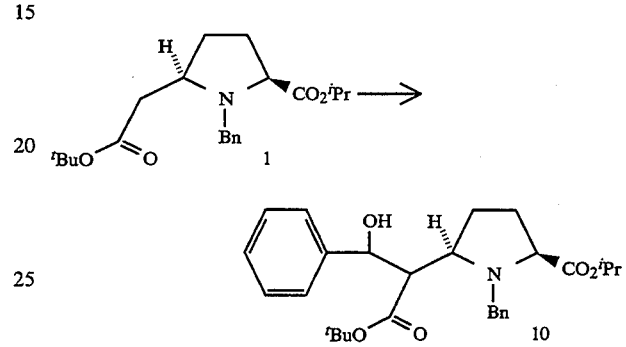

In the same manner as in Example 11, Compound 1 (365 mg, 1.01 mmol) was reacted with benzaldehyde (0.14 ml, 1.4 mmol).

The reaction mixture was purified by a medium pressure silica gel column chromatography (Lobar size B, ethyl acetate-hexane 1:6) to recover the unreacted starting material (Compound 1, 65 mg, 18%) as well as to obtain a mixture of three isomers of Compound 10 (Compounds 10a, 10b and 10c (13:27:60), colorless viscous material, 325 mg, Spectrum data of an isomer of isopropyl (2S,5R)-1-benzyl-5-[(1R)-2-hydroxy-2-phenyl-1-(t-butoxycarbonyl)ethyl]pyrrolidine-2-carboxylate (Compound 10a);

NMR: 1.09 (3H, d, J=6.0), 1.14 (3H, d, J=6.3), 1.27 (9H, s), 1.81–2.14 (4H, m, 3-CH₂ and 4-CH₂), 2.88 (1H, dd, J=8.7, 3.9, 6-CH), 3.35–3.48 (2H, m, 2-CH and 5-CH), 3.83 (1H, d, J=13.5), 3.99 (1H, br, OH), 4.18 (1H, d, J=13.5), 4.85 (1H, sept, J=6.3), 5.32 (1H, br, 8-CH), 7.15–7.45 (10H, m).

Spectrum data of an isomer of isopropyl (2S,5R)-1-benzyl-5-[(1S)-2-hydroxy-2-phenyl-1-(t-butoxycarbonyl)ethyl]pyrrolidine-2-carboxylate (Compound 10b);

NMR: 1.11 (3H, d, J=6.3), 1.15 (9H, s), 1.17 (3H, d, J=6.0), 1.94–2.15 (4H, m, 3-CH₂ and 4-CH₂), 2.92 (1H, dd, J=8.0, 2.9, 6-CH), 3.39 (1H, dd, J=7.2, 5.4, 2-CH), 3.62 (1H, dr, J=8.0, ca. 7, 5-CH), 3.72 (1H, d, J=14.3), 3.97 (1H, d, J=14.3), 4.38 (1H, br-d, J=ca. 10, OH), 4.88 (1H, sept, J=6.3), 5.12 (1H, br-m, 8-CH), 7.15–7.45 (10H, m).

Spectrum data of the other isomer of isopropyl (2S,5R)-1-benzyl-5-[(1S)-2-hydroxy-2-phenyl-1-(t-butoxycarbonyl)ethyl]pyrrolidine-2-carboxylate (Compound 10c);

NMR: 1.0 (3H, d, J=6.3), 1.11 (3H, d, J=6.3 ), 1.13 (9H, s), 1.94–2.20 (3H, m, 3-CH₂ and 4-CH), 2.36–2.50 (1H, m, 4-CH), 3.06 (1H, dd, J=10.2, 3.3, 6-CH), 3.36 (1H, ddd, J=ca. 8, ca. 7, 3.3, 5-CH), 3.42 (1H, dd, J=8.7, 5.7, 2-CH), 3.72 (1H, d, J=12.9), 4.14 (1H, d, J=12.9), 4.83 ( 1H, sept, J=6.3), 5.13 (1H, d, J=10.2, 8-CH), 6.77 (1H, s, OH), 7.2–7.45 (10H, m).

EXAMPLE 19

Synthesis of Isopropyl (2S,5R)-1-Benzyl-5-[2-Hydroxy-2-(2-Furyl)-1-(t-Butoxycarbonyl)Ethyl]Pyrrolidine-2-Carboxylate (Compound 11)

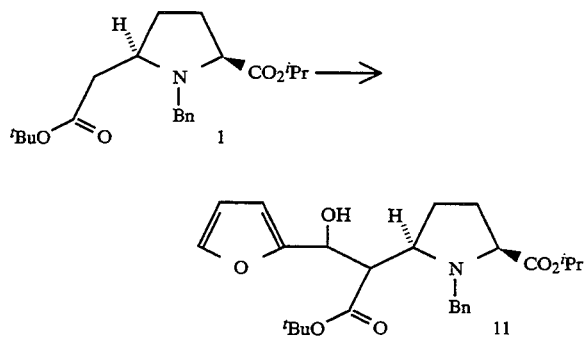

In the same manner as in Example 11, Compound 1 (365 mg, 1.01 mmol) was reacted with furfural (0.116 ml, 1.4 mmol).

The reaction mixture was purified by a medium pressure silica gel column chromatography (Lobar size B, ethyl acetate-hexane 1:6) to recover the unreacted starting material (Compound 1, 27 mg, 7%) as well as to obtain a mixture of two isomers of Compound 11 (Compounds 11a and 11b (56: 44), colorless viscous material, 109 mg, 24%) and the other isomer (Compound 11c, colorless viscous material, 223 mg, 48%).

Spectrum data of Compound 11a;

NMR: 1.11 (3H, d, J=6.3), 1.15 (3H, d, J=6.0), 1.37 (9H, s), 1.8–2.1 (4H, m, 3-$CH_2$ and 4-$CH_2$), 3.05 (1H, dd, J=6.6, 2.7, 6-CH), 3.37 (1H, m, 2-CH), 3.56 (1H, m, 5-CH), 3.69 (1H, d, J=13.7), 3.97 (1H, d, J=13.7), 4.84 (1H, sept, J=6.3), 4.86 (1H, br, OH), 5.25 (1H, br, 8-CH), 6.23–6.33 (2H, m), 7.2–7.4 ( 6H, m).

Spectrum data of Compound 11b;

NMR: 1.05 (3H, d, J=6.3), 1.10 (3H, d, J=6.3), 1.42 (9H, s), 1.8–2.1 (4H, m, 3-$CH_2$ and 4-$CH_2$), 2.98 (1H, dd, J=9.6, 3.9, 6-CH), 3.37 (1H, m, 2-CH), 3.56 (1H, m, 5-CH), 3.72 (1H, d, J=13.4), 4.13 (1H, d, J=13.4), 4.79 (1H, sept, J=6.3), 5.06 (1H, br, OH), 5.32 (1H, br, 8-CH), 6.23–6.33 (2H, m), 7.2–7.4 ( 6H, m).

Spectrum data of Compound 11c;

IR (neat): 3277, 1728 $cm^{-1}$.

NMR: 1.09 (3H, d, J=6.0), 1.10 (3H, d, J=6.3), 1.26 (9H, s), 1.87–2.35 (4H, m, 3-$CH_2$ and 4-$CH_2$), 3.35–3.45 (3H, m, 2-CH and 5-CH and 6-CH), 3.68 (1H, d, J=13.2), 4.18 (1H, d, J=13.2), 4.80 (1H, sept, J=6.3), 5.25 (1H, d, J=10.2, 8-CH), 6.27–6.33 (2H, m), 6.77 (1H, s, OH), 7.2–7.4 (6H, m).

EXAMPLE 20

Synthesis of Isopropyl (2S,5R)-1-Benzyl-5-[2-Hydroxy-2-(2-Pyridyl)-1-(t-Butoxycarbonyl)Ethyl]Pyrrolidine-2-Carboxylate (Compound 12)

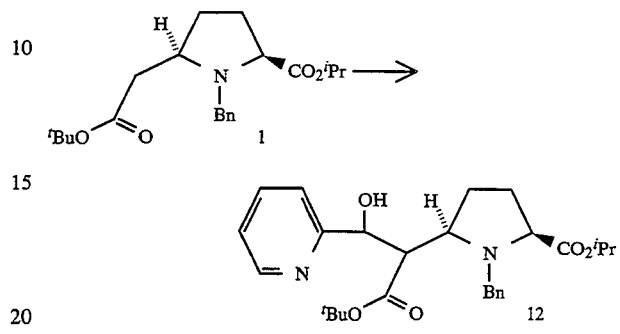

In the same manner as in Example 11, Compound 1 (365 mg, 1.01 mmol) was reacted with pyridine-2-carboxaldehyde (0.135 ml, 1.4 mmol).

The reaction mixture was purified by a medium pressure silica gel column chromatography (Lobar size B, ethyl acetate-hexane 1:6→1:1) to recover the unreacted starting material (Compound 1, 64 mg, 18%) as well as to obtain a mixture of two isomers of Compound 12 (Compounds 12a and 12b (61:39), colorless viscous material, 125 mg, 26%) and other two isomers (Compounds 12c, yellow viscous material, 156 mg, 33% and Compounds 12d, yellow viscous material, 29 mg, 6%).

Spectrum data of Compound 12a;

NMR: 1.07 (3H, d, J=6.3), 1.14 (3H, d, J=6.3), 1.17 (9H, s), 1.9–2.3 (4H, m, 3-$CH_2$ and 4-$CH_2$), 3.21 (1H, dd, J=6.8, 2.6, 6-CH), 3.41 (1H, dd, J=7.8, 5.4, 2-CH), 3.64 (1H, m, 5-CH), 3.74 (1H, d, J=14.1), 4.07 (1H, d, J=14.1), 4.84 (1H, sept, J=6.3), 5.17 (1H, br, OH), 5.33 (1H, br, 8-CH), 7.17.4 (7H, m), 7.64 (1H, m), 8.50 (1H, m).

Spectrum data of Compound 12b;

NMR: 1.05 (3H, d, J=6.3), 1.11 (3H, d, J=6.3), 1.23 (9H, s), 1.8–2.3 (4H, m, 3-$CH_2$ and 4-$CH_2$), 3.06 (1H, dd, J=8.1, 3.3, 6-CH), 3.42 (1H, 2-CH), 3.72 (1H, m, 5-CH), 3.76 (1H, d, J=13.4), 4.21 (1H, d, J=13.4), 4.80 (1H, sept, J=6.3), 5.21 (1H, br, OH), 5.46 (1H, br, 8-CH), 7.1–7.4 (6H, m), 7.58 (1H, m), 7.68 (1H, m), 8.53 (1H, m).

Spectrum data of Compound 12c;

IR (neat): 3282, 1727 $cm^{-1}$.

NMR: 1.10 (3H, d, J=6.3), 1.11 (3H, d, J=6.3), 1.22 (9H, s), 1.89–2.18 (3H, m, 3-$CH_2$ and 4-CH), 2.30–2.43 (1H, m, 4-CH), 3.42 (1H, dd, J=8.7, 6.0, 2-CH), 3.47 (1H, m, 5-CH), 3.50 (1H, dd, J=10.2, 3.3, 6-CH), 3.72 (1H, d, J=13.2), 4.19 (1H, d, J=13.2), 4.83 (1H, sept, J=6.3), 5.31 (1H, d, J=10.2, 8-CH), 6.91 (1H, br, OH), 7.17 (1H, m), 7.2–7.4 (5H, m), 7.49 (1H, m), 7.67 (1H, m), 8.55 (1H, m).

Spectrum data of Compound 12d;

IR (neat): 3400, 1725 $cm^{-1}$.

NMR: 1.06 (3H, d, J=6.0), 1.10 (3H, d, J=6.3), 1.17 (9H, s), 1.77–1.85 (1H, m, 4-CH), 1.90–2.08 (2H, m, 3-CH and 4-CH), 2.11–2.21 (1H, m, 3-CH), 2.81 (1H, t, J=9.0, 6-CH), 3.45 (1H, t, J=8.0, 2-CH), 3.75 (1H, m, 5-CH), 3.77 (1H, d, J=12.5), 4.26 (1H, d, J=12.5), 4.78 (1H, sept, J=6.3), 5.09 (1H, d, J=9.0, 8-CH), 6.97 (1H, br, OH), 7.17 (1H, m), 7.2–7.42 (5H, m), 7.55 (1H, m), 7.68 (1H, m), 8.52 (1H, m).

EXAMPLE 21

Synthesis of Isopropyl (2S,5R)-1-Benzyl-5-(t-Butoxycarbonylmethyl)Pyrrolidine-2-Carboxylate (Compound 1)

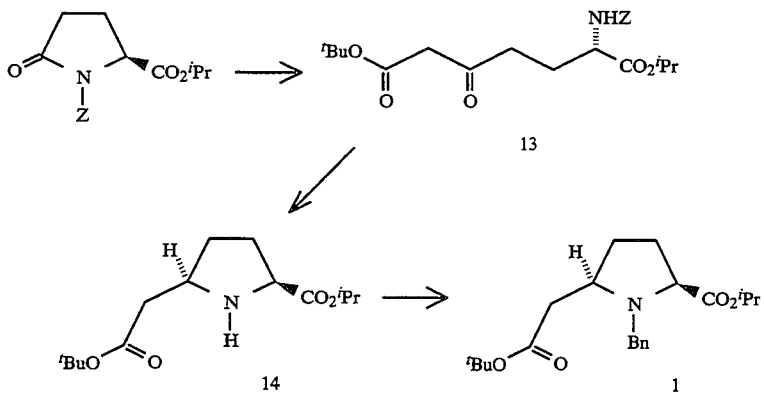

1) Under an argon atmosphere, n-butyl lithium (1.56M/hexane, 46.2 ml, 72 mmol) was added dropwise to a THF (250 ml) solution of diisopropylamine (11.0 ml, 78.5 mmol) at −60° C. and the mixture was stirred at the same temperature for 5 minutes and under ice-cooling for 20 minutes. To the solution was added dropwise a THF (15 ml) solution of t-butyl acetate (9.7 ml, 72 mmol) at −65° C., and the mixture was stirred for 30 minutes. Subsequently, a THF (25 ml) solution of isopropyl N-benzyloxycarbonyl-L-pyrroglutamate was added dropwise and the mixture was stirred for 60 minutes.

The reaction was stopped by adding 20 ml of an aqueous 20% ammonium chloride solution, the organic layer was separated, the aqueous layer was extracted with ethyl acetate, and the organic layers were combined, washed with NaCl-saturated water and dried. The solvent was removed by distillation under reduced pressure. The solvent was sufficiently removed with a vacuum pump. Isopropyl (2S)-2-(benzyloxycarbonylamino)-6-(t-butoxycarbonyl)-5-oxohexanoate (Compound 13) was obtained as a pale yellowish viscous liquid (27.68 g, 100%).

Spectrum date of Compound 13;
NMR: 1.20–1.30 (6H, m), 1.46 (9H, s), 1.85–1.99 (1H, m, 3-CH), 2.10–2.26 (1H, m, 3-CH), 2.52–2.77 (2H, m, 4-CH$_2$), 3.33 (2H, s, 6-CH$_2$), 4.30 (1H, m, 2-CH), 4.97–5.1 (1H, m), 5.10 (2H, s), 5.37 (1H, br-d, NH), 7.25–7.4 (5H, m).

2) Acetic acid (7.5 ml, 130 mmol) was added to an isopropyl alcohol (200 ml) solution of Compound 13 (27.68 g, 65.5 mmol), and the mixture was subjected to hydrogenolysis using 10% palladium carbon (650 mg) as the catalyst at atmospheric pressure for 37 hours. Subsequently, platinum oxide (370 mg) was added and the mixture was reduced again with hydrogen under atmospheric pressure for 128 hours (during this procedure, acetic acid (3.2 ml) and platinum oxide (100 mg) were further added).

The catalyst was filtered and the filtrate was concentrated to about 100 ml under reduced pressure. Then, sodium hydrogen carbonate (30 g, 357 mmol) and water (40 ml) were added to the residue and the mixture was stirred. When evolution of a gas became weak, water (20 ml) was further added. The remaining isopropyl alcohol was removed by distillation under reduced pressure, followed by addition of water (20 ml), and the resulting mixture was extracted with ethyl acetate. The ethyl acetate solution was washed with an aqueous NaCl-saturated solution, and dried. The solvent was removed by distillation under reduced pressure. Isopropyl (2S,5R)-5-(t-butoxycarbonylmethyl)pyrrolidine-2-carboxylate (Compound 14) was obtained as a yellowish liquid (17.05 g, 96%).

Spectrum data of Compound 14;
IR (neat): 1730 cm$^{-1}$.
NMR: 1.24 (3H, d, J=6.3), 1.25 (3H, d, J=6.3), 1.45 (9H, s), 1.34–1.5 (1H, m, 4-CH), 1.84–1.99 (2H, m, 3-CH and 4-CH), 2.02–2.15 (1H, m, 3-CH), 2.42 (1H, dd, J=15.5, 6.2, 6-CH), 2.50 (1H, dd, J=15.5, 7.4, 6-CH), 3.42 (1H, m, 5-CH), 3.72 (1H, dd, J=8.7, 5.7, 2-CH), 5.03 (1H, sept, J=6.3).

3) Under a dry atmosphere, triethylamine (9.6 ml, 69 mmol) was added to a dichloromethane (200 ml) solution of Compound 14 (17.0 g, 62.6 mmol), and a dichloromethane (20 ml) solution of benzyl bromide (9.0 ml, 76 mmol) was also added dropwise at room temperature. The mixture was stirred for 43 hours. During this procedure, benzyl bromide (0.75 ml) was further added two times.

The solvent was removed by distillation under reduced pressure, ethyl acetate (200 ml) was added, and the mixture was washed with an aqueous 5% sodium hydrogen carbonate solution and an aqueous NaCl-saturated solution, and dried. The solvent was removed by distillation under reduced pressure. The residue was purified by a silica gel column chromatography (70 $\phi \times 160$ mm, ethyl acetate-hexane 0:100→7:93) to obtain Compound 1 as a colorless liquid (19.58 g, 86%).

Spectrum data of Compound 1;
IR (neat): 1729 cm$^{-1}$.
NMR: 1.10 (3H, d, J=6.3), 1.15 (3H, d, J=6.3), 1.42 (9H, s), 1.62–1.75 (1H, m, 4-CH), 1.81–2.08 (3H, m, 3-CH$_2$ and 4-CH), 2.24 (1H, dd, J=14.9, 9.2, 6-CH), 2.54 (1H, dd, J=14.9, 4.4, 6-CH), 3.16 (1H, m, 5-CH), 3.30 (1H, dd, J=7.9, 6.6, 2-CH), 3.77 (1H, d, J=14.0), 3.89 (1H, d, J=14.0), 4.86 (1H, sept, J=6.3), 7.2–7.35 (5H, m).

EXAMPLE 22

Synthesis of Methyl (2S,5R)-1-Benzyl-5-(t-Butoxycarbonylmethyl)Pyrrolidine-2-Carboxylate (Compound 3)

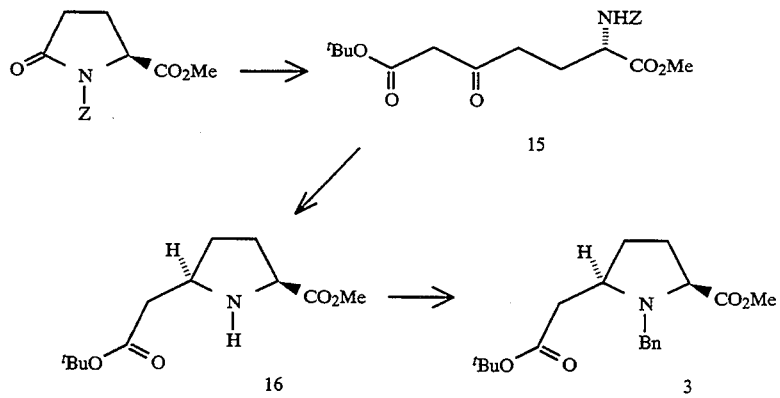

1) In the same manner as in Example 27-1), methyl N-benzyloxycarbonyl-L-pyrroglutamate was reacted with t-butyl acetate to obtain methyl (2S)-2-(benzyloxycarbonylamino)-6-(t-butoxycarbonyl)-5-oxohexanoate (Compound 15) as a pale yellowish viscous liquid (yield 90 to 100%).

Spectrum data of Compound 15;
NMR: 1.46 (9H, s), 1.87–2.01 (1H, m, 3-CH), 2.10–2.27 (1H, m, 3-CH), 2.514–2.75 (2H, m, 4-CH$_2$), 3.33 (2H, s, 6-CH$_2$), 3.74 (3H, s), 4.35 (1H, m, 2-CH), 5.10 (2H, s), 5.39 (1H, br-d, NH), 7.25–7.4 (5H, m).

2) In the same manner as in Example 27-2), Compound (5.08 g, 12.9 mmol) was reacted, except that methanol was used as a solvent.

Methyl (2S,5R)-5-(t-butoxycarbonylmethyl)pyrrolidine-2-carboxylate (Compound 16) was obtained as a yellowish liquid (2.69 g, 86%).

Spectrum data of Compound 16;
NMR: 1.45 (9H, s), 1.33–1.5 (1H, m, 4-CH), 1.88–2.00 (2H, m, 3-CH and 4-CH), 2.04–2.17 (1H, m, 3-CH), 2.44 (1H, dd, J=15.6, 6.0, 6-CH), 2.48 (1H, dd, J=15.6, 7.2, 6-CH), 3.43 (1H, m, 5-CH), 3.72 (3H, s), 3.79 (1H, dd, J=9.0, 6.0, 2-CH).

3) In the same manner as in Example 27-3), Compound (622 mg, 2.56 mmol) was reacted (room temperature, 27 hours).

The product was purified by a medium pressure silica gel column chromatography (Lobar size B, ethyl acetate-hexane 1:5). Compound 3 was obtained as a colorless liquid (649 mg, 76%).

Spectrum data of Compound 3;
Mass spectrum m/z=333 (M+).
IR (neat): 1729 cm$^{-1}$.

NMR: 1.43 (9H, s), 1.65–1.77 (1H, m, 4-CH), 1.84–2.08 (3H, m, 3-CH$_2$ and 4-CH), 2.27 (1H, dd, J=14.8, 9.1, 6-CH), 2.58 (1H, dd, J=14.8, 4.3, 6-CH), 3.14 (1H, m, 5-CH), 3.33 (1H, dd, J=ca.7, ca.8, 2-CH), 3.38 (3H, s), 3.70 (1H, d, J=13.9), 3.93 (1H, d, J=13.9), 7.2–7.35 (5H, m).

EXAMPLE 23

Synthesis of Isopropyl (2S,5R)-1-Benzyl-5-(Methoxycarbonylmethyl)Pyrrolidine-2-carboxylate (Compound 5)

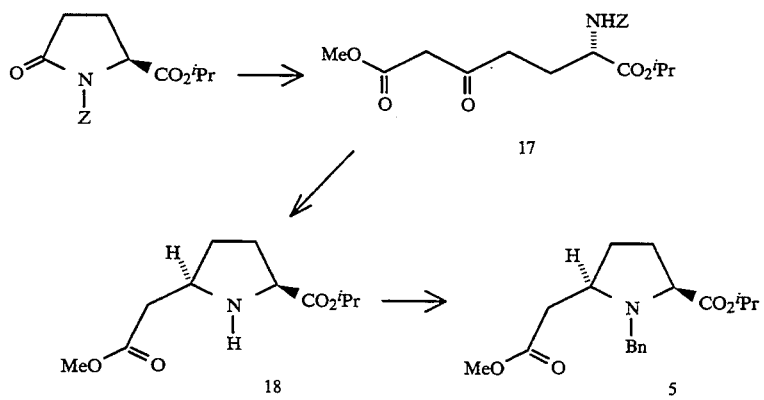

1) In the same manner as in Example 27-1), isopropyl N-benzyloxycarbonyl-L-pyrroglutamate (2.01 g, 6.58 mmol) was reacted with methyl acetate.

2.46 g of a crude isopropyl (2S)-2-(benzyloxycarbonylamino)-6-(methoxycarbonyl)-5-oxohexanoate (Compound 17) product was obtained as a yellowish viscous liquid, (which product contained about 9% of impurities and, as Compound 17, 2.28 g, 91%).

Spectrum data of Compound 17;
IR (neat): 3359, 1723 cm$^{-1}$.
NMR: 1.22–1.30 (6H, m), 1.83–1.99 (1, m, 3-CH), 2.12–2.30 (1H, m, 3-CH), 2.50–2.77 (2H, m, 4-CH$_2$), 3.44 (2H, s, 6-CH$_2$), 3.72 (3H, s), 4.30 (1H, m, 2-CH), 4.97–5.1 (1H, m), 5.11 (2H, s), 5.37 (1H, br-d, NH), 7.25–7.4 (5H, m).

2) In the same manner as in Example 27-2), Compound 17 (2.46 g, as Compound 17, 2.28 g, 6.01 mmol)

was reacted, except that when extraction with ethyl acetate was carried out, NaCl and sodium hydrogen carbonate were excessively added to an aqueous layer and the mixture was sufficiently extracted.

1.30 g of a crude isopropyl (2S,5R)-5-(methoxycarbonylmethyl)pyrrolidine-2-carboxylate (Compound 18) product was obtained as a yellowish liquid, (which product contained about 21% of impurities and, as Compound 19, about 1.03 g, 74%).

Spectrum data of Compound 18;
NMR: 1.24 (3H, d, J=6.2), 1.25 (3H, d, J=6.4), 1.35-1.48 (1H, m, 4-CH), 1.87-2.02 (2H, m, 3-CH and 4-CH), 2.04-2.17 (1H, m, 3-CH), 2.53 (1H, dd, J=15.8, 6.0, 6-CH), 2.58 (1H, dd, J=15.8, 7.5, 6-CH), 3.49 (1H, m, 5-CH), 3.69 (3H, s), 3.74 (1H, dd, J=8.7, 5.6, 2-CH), 5.03 (1H, sept, J=6.3).

3) In the same manner as in Example 27-3), Compound 18 (1.30 g, as Compound 18, 1.03 g, 4.49 mmol) was reacted (room temperature, 28 hours).

The product was purified by a medium pressure silica gel column chromatography (Lobar size B, ethyl acetatehexane 1:5). Compound 5 was obtained as a colorless liquid. 1.228 g (86%).

Spectrum data of Compound 5;
IR (neat): 1735 cm$^{-1}$.
NMR: 1.11 (3H, d, J=6.3), 1.16 (3H, d, J=6.3), 1.62-1.74 (1H, m, 4-CH), 1.82-2.10 (3H, m, 3-CH$_2$ and 4-CH), 2.35 (1H, dd, J=15.3, 9.0, 6-CH), 2.58 (1H, dd, J=15.3, 4.5, 6-CH), 3.22 (1H, m, 5-CH), 3.33 (1H, dd, J=7.8, 6.7, 2-CH), 3.63 (3H, s), 3.83 (2H, ABq, J=14.0), 4.87 (1H, sept, J=6.3), 7.2-7.35 (5H, m).

In the following, a series of reaction steps (Reference example 1) for obtaining (5R, 6R)-6-(2-hydroxy-2-propyl)-2-[(3S)-pyrrolidine-3-ylthio]-1-carba-2-penem-3-carboxylic acid (Compound S9) from isopropyl (2S,5R)-1-benzyl-5-[(R)-2-hydroxy-2-methyl-1-(t-butoxycarbonyl)propyl]pyrrolidine-2-carboxylate (Compound 2a) and another series of reaction steps (Reference example 2) for obtaining p-nitrobenzyl (5R,6R)-6-[(R)-1-hydroxyethyl]-2-[(3S)-1-(p-nitrobenzyloxycarbonyl)pyrrolidine-3-ylthio]-1-carba-2-penem-3-carboxylate (Compound S16) from isopropyl (2S,5R)-1-benzyl-5-[(1S,2R)-2-hydroxy-1-(t-butoxycarbonyl)-propyl]pyrrolidine-2-carboxylate (Compound 8b) are exemplified for reference purpose.

In addition to the abbreviations used in Examples 11 to 29, the following are used.
DBU: 1,8-Diazabicyclo[5,4,0]-7-undecene
DMF: N,N-Dimethylformamide
PNB: Para-nitrobenzyl
PNZ: Para-nitrobenzyloxycarbonyl

REFERENCE EXAMPLE 1

(a) Synthesis of Isopropyl (3S,5R,6R)-6-(2-Hydroxy-2-Propyl)-1-Carbapenam-3-Carboxylate (Compound S1)

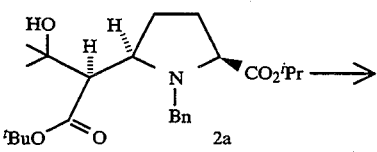

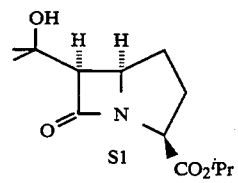

Acetic acid (0.42 ml, 7.3 mmol) was added to a methanol (27 ml) solution of a mixture of Compounds 2a and 2b (29:71), (3.08, 7.34 mmol), and the mixture was subjected to hydrogenolysis using a 10% palladium carbon (120 mg) as the catalyst at atmospheric pressure for 7 hours.

The catalyst was removed by filtration, and the solvent was removed by distillation under reduced pressure. The residue was dissolved in ethyl acetate, and the solution was washed with an aqueous 5% sodium hydrogen carbonate solution. The aqueous layer was reverse-extracted with ethyl acetate. The ethyl acetate solutions were combined, washed with an aqueous NaCl-saturated solution and dried, and the solvent was removed by distillation under reduced pressure. The N-deprotected material was obtained as a pale yellowish viscous liquid. 2.33 g (96.5%).

Under a dry atmosphere, to a dichloromethane (3 ml) solution of this N-deprotected material was added 4N hydrochloride/dioxane (30 ml) under ice-cooling, and the mixture was stirred at room temperature for 23 hours. The solvent was removed by distillation under reduced pressure, and hexane was added to the residue and removed by distillation under reduced pressure (three times). Evaporation with a vacuum pump gave a pale yellowish foamy solid (2.56 g). Under a dry atmosphere, to a dichloromethane (50 ml) solution of this foamy material were added triethylamine (1.3 ml, 9.3 mmol) and water-soluble carbodiimide (1-ethyl-3-[3-(dimethylamino)propyl]carbodiimide hydrochloride (1.8 g, 9.4 mmol) under ice-cooling, and the mixture was stirred at room temperature for 12.5 hours. The solvent was removed by distillation under reduced pressure, water was added and the mixture was extracted with ethyl acetate. The ethyl acetate solution was washed with an aqueous NaCl-saturated solution and dried, and the solvent was removed by distillation under reduced pressure.

The residue was divided into two portions. Each portion was purified by a medium pressure silica gel column chromatography (Lobar size B, ethyl acetate-hexane 1:1) to obtain Compound S1 (pale yellowish fine needle crystals, top. 69°-70.5° C., 416 mg, yield from Compound 2a, 77%), and the 6-position isomer derived from Compound 2b ((3S,5R,6S)isomer, pale yellowish viscous liquid, 944 mg, yield from Compound 2b, 71%).

Spectrum date of Compound S1;
IR (KBr): 3450, 3520, 1740, 1720 cm$^{-1}$.
NMR: 1.25 (3H, d, J=6.3), 1.27 (3H, s), 1.30 (3H, d, J=6.2), 1.47 (3H, s), 1.88 (1H, m, 1-CH), 2.23-2.33 (2H, m, 2-CH$_2$), 2.53 (1H, s, OH), 2.85 (1H, m, 1-CH), 3.23 (1H, dd, J=5.1, 1.1, 6-CH), 3.77 (1H, dt, J=9.8, 5.5, 5-CH), 3.89 (1H, m, 3-CH), 5.09 (1H, sept, J=6.3).

(b) Synthesis of Isopropyl (5R,6R)-6-(2-Hydroxy-2-Propyl)-3-Phenylseleno-1-Carbapenam-3-Carboxylate (Compound S2)

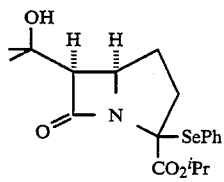

Under an argon atmosphere, n-butyl lithium (1.6M/hexane, 1.9 ml, 3.0 mmol) was added to a THF (9 ml) solution of diisopropylamine (0.46 ml, 3.3 mmol) at −70° C., and the mixture was stirred for 30 minutes. To the solution was added dropwise a THF (3 ml) solution of Compound S1 (308 mg, 1.21 mmol) at −70° C., and the mixture was stirred for 26 minutes. Subsequently, a THF (2 ml) solution of phenylselenyl chloride (350 mg, 1.8 mmol) was added dropwise and the mixture was stirred for 5 minutes.

The reaction was stopped by adding an aqueous 10% ammonium chloride solution (18 ml). The reaction mixture was extracted with ethyl acetate, the ethyl acetate solution was washed with an aqueous NaCl-saturated solution and dried, and the solvent was removed by distillation under reduced pressure. The residue was purified by a medium pressure silica gel column chromatography (Lobar size B, ethyl acetate-hexane 1:2) to obtain a mixture of the two isomers of Compound S2 (78:22, yellowish viscous material, 343 mg, 69%).

Spectrum date of Compound S2;

NMR of low polarity isomer: 1.21 (3H, s), 1.27 (6H, d, J=6.3), 1.44 (3H, s), 1.80–1.93 (1H, m, 1-CH), 1.92 (1H, s, OH), 2.25–2.36 (1H, m, 2-CH), 2.61–2.81 (2H, m, 1-CH and 2CH), 3.22 (1H, d, J=5.7, 6-CH), 3.53 (1H, m, 5-CH), 5.09 (1H, sept, J=6.3), 7.25–7.4 (3H, m), 7.6–7.7 (2H, m).

NMR of high polarity isomer: 1.13 (3H, d, J=6.3), 1.14 (3H, d, J=6.3), 1.29 (3H, s), 1.53 (3H, s), 1.81 (1H, s, OH), 1.85–1.96 (1H, m, 1-CH), 2.40–2.59 (2H, m, 2-CH$_2$), 2.90 (1H, m, 1-CH), 3.25 (1H, d, J=5.4, 6-CH), 3.87 (1H, m, 5-CH), 4.81 (1H, sept, J=6.3), 7.25–7.4 (3H, m), 7.7.–7.8 (2H, m).

(c) Synthesis of Isopropyl (5R,6R)-6-(2-Hydroxy-2-Propyl-1-Carba-2-Penem-3-Carboxylate (Compound S3)

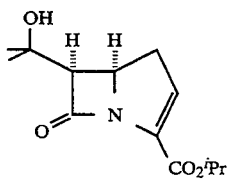

Under an argon atmosphere, to a dichloromethane (10 ml) solution of Compound S2 (two isomers (78:22), 343 mg, 0.836 mmol) was added dropwise a dichloromethane (3.5 ml) solution of meta-chloroperbenzoic acid (320 mg, 1.8 mmol) at −30° C. and the mixture was stirred for 30 minutes. Subsequently, at the same temperature, triethylamine (0.35 ml, 2.5 mmol) was added dropwise and the mixture was stirred for 30 minutes.

The reaction mixture was diluted with ethyl acetate, washed with water, and the aqueous layer was reverse-extracted with ethyl acetate. The ethyl acetate solutions were combined, washed with an aqueous NaCl-saturated solution and dried, and the solvent was removed by distillation under reduced pressure. The residue was purified by a medium pressure silica gel column chromatography (Lobar size B, ethyl acetate-hexane 1:2→1:1) to obtain Compound S3 (colorless crystals, mp. 108°–110° C., 149 mg, 70%).

Spectrum data of Compound S3;

IR (KBr): 3450, 1770, 1750, 1720, 1680 cm$^{-1}$.

NMR: 1.27 (3H, s), 1.31 (3H, d, J=6.3), 1.32 (3H, d, J=6.5), 1.51 (3H, s), 1.61 (1H, s, OH), 2.67 (1H, ddd, J=18.7, 10.1, 3.1, 1-CH), 3.59 (1H, d, J=6.1, 6-CH), 3.78 (1H, ddd, J=18.7, 9.0, 2.6, 1-CH), 4.32 (1H, ddd, J=10.1, 9.0, 6.1, 5-CH), 5.15 (1H, sept, J=6.3), 6.52 (1H, dd, J=3.1, 2.6, 2-CH), minute coupling (<1 Hz) was admitted between 2-CH and 6-CH.

(d) Synthesis of Isopropyl (5R,6R)-6-(2-Hydroxy-2-Propyl)-2-Ethylthio-1-Carbapenam-3-Carboxylate (Compound S4)

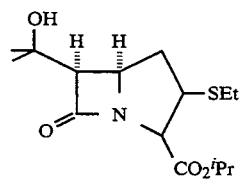

Under a dry atmosphere, to a dichloromethane (9 ml) solution of Compound S3 (149 mg, 0.588 mmol) were added ethanethiol (0.094 ml, 1.3 mmol) and DBU (0.040 ml, 0.27 mmol) at −30° C., and the mixture was stirred at the same temperature for 80 minutes.

The reaction mixture was diluted with ethyl acetate, washed with an aqueous 5% citric acid solution, an aqueous sodium hydrogen carbonate solution and an aqueous NaCl-saturated solution, and dried. The solvent was removed by distillation under reduced pressure to obtain a mixture of two isomers of Compound S4 (71:29, pale yellowish viscous material, 177 mg, 95%).

(e) Synthesis of p-Nitrobenzyl (5R,6R)-6-(2-Hydroxy-2-Propyl)-2-Ethylthio-1-Carbapenam-3-Carboxylate (Compound S5)

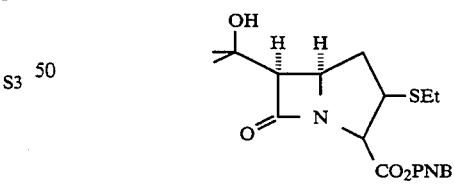

To a THF-water (2:1, 9 ml) solution of Compound S4 (two isomers (72:28), 239 mg, 0.758 mmol) was added under ice-cooling an aqueous 1N sodium hydroxide solution (0.758 ml, 0.758 mmol) in consecutive 5 portions at every 8 minutes. The mixture was stirred under ice-cooling for 30 minutes and at room temperature for 3 hours. Water (3 ml) was added, the THF was removed by distillation under reduced pressure and the residual aqueous solution was washed with ether (from the ether solution, Compound S4 (72 mg, 30%) was recovered).

Water was removed by distillation under reduced pressure to dryness. Under a dry atmosphere, para-nitrobenzyl bromide (180 mg, 0.83 mmol) was added to a DMF (7 ml) solution of the residue (pale yellowish candy-like material), and the mixture was stirred at room temperature for 3.8 hours. The DMF was removed by distillation under reduced pressure, the residue was diluted with ethyl acetate and washed with an aqueous NaCl-semisaturated solution. The aqueous layer was reverse-extracted with ethyl acetate, the ethyl acetate solutions were combined, washed with an aqueous NaCl-saturated solution and dried, and the solvent was removed by distillation under reduced pressure. The residue was purified by a medium pressure silica gel column chromatography (Lobar size B, ethyl acetate-hexane 1:2→1:1) to obtain an isomer of Compound S5 (pale yellowish viscous material, 103 mg, 33%).

Spectrum data of Compound S5;

NMR: 1.22 (3H, t, J=7.5), 1.25 (3H, s), 1.48 (3H, s), 1.72 (1H, s, OH), 2.34 (1H, m, 1-CH), 2.57 (2H, q, J=7.5, SCH$_2$), 2.87 (1H, ddd, J=12.8, 11.8, 9.7, 1-CH), 3.42 (1H, d, J=5.4, 6-CH), 3.72 (1H, ddd, J=11.8, 8.7, 6.5, 2-CH), 3.92 (1H, m, 5-CH), 4.22 (1H, d, J=8.7, 3-CH), 5.31 (2H, ABq, J=13.4), 7.56 (2H, d), 8.24 (2H, d).

(f) Synthesis of p-Nitrobenzyl (5R,6R)-6-(2-Hydroxy-2-Propyl)-2-Chloro-2-Ethanesulfinyl-1-Carbapenam-3-Carboxylate (Compound S6)

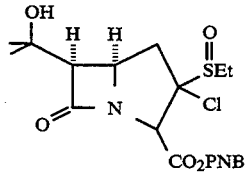

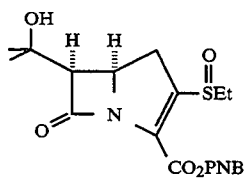

Under a dry atmosphere, to a dichloromethane (4 ml) solution of Compound S5 (50 mg, 0.12 mmol) were added water (0.011 ml, 0.61 mmol) and pyridine (0.030 ml, 0.37 mmol), and further added dropwise a dichloromethane (1.5 ml) solution of iodobenzene dichloride (84 mg, 0.31 mmol) under ice-cooling, and the mixture was stirred at the same temperature for 30 minutes. Subsequently, triethylamine (0.034 ml, 0.24 mmol) was added and the mixture was stirred for 10 minutes.

The reaction mixture was diluted with ethyl acetate, washed with water and an aqueous NaCl-saturated solution and dehydrated, and the solvent was removed by distillation under reduced pressure. The residue was purified by a medium pressure silica gel column chromatography (Lobar size A, ethyl acetate-hexane 1:1→1:0) to obtain a mixture (pale yellowish viscous material, 58 mg) of some isomers of Compound S6 and a little amount of p-nitrobenzyl (5R,6R)-6-(2-hydroxy-2-propyl)-2-ethanesulfinyl-1-carba-2-penem-3-carboxylate (Compound S7).

The facts that Compound S6 is a mixture of the isomers and Compound S7 is mixed therewith have no problem since these compounds are all converted into the same compound in the next step.

(g) Synthesis of p-Nitrobenzyl (5R,6R)-6-(2-Hydroxy-2-Propyl)-2-[(3S)-1-(p-Nitrobenzyloxycarbonyl)Pyrrolidine-3-Ylthiol-1-Carba-2-Penem-Carboxylate (Compound S8)

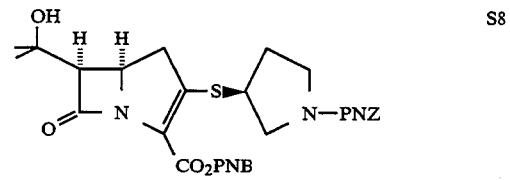

Under an argon atmosphere, DBU (0.014 ml, 0.094 mmol) was added to a DMF (3 ml) solution of a mixture (44 mg, 50 mg obtained from Compound S5) of Compounds S6 and S7 at −30° C., and the mixture was stirred for 34 minutes. Subsequently, at the same temperature, a DMF (0.15 ml) solution of (S)-3-mercapto-1-(p-nitrobenzyloxycarbonyl)pyrrolidine (33 mg, 0.12 mmol) was added, and the mixture was stirred for 40 minutes.

An aqueous 5% citric acid solution was added, and the mixture was extracted with ethyl acetate. The ethyl acetate solution was washed with an aqueous NaCl-semisaturated solution and an aqueous NaCl-saturated solution, and dried. The solvent was removed by distillation under reduced pressure. The residue was purified by a medium pressure silica gel column chromatography (Lobar size A, ethyl acetate-hexane 2:1) to obtain Compound S8. Yellowish viscous material, 41 mg. The material contained DMF (about 0.5 mg) and ethyl acetate (about 3.5 mg), and it is 37 mg as Compound S8. Yield from Compound S5, 48%.

Spectrum data of Compound S8;

IR (neat): 3417, 1778, 1707 cm$^{-1}$.

NMR: 1.29 (3H, s), 1.54 (3H, s), 1.5–1.7 (br, OH), 1.93–2.09 (1H, br, 4'-CH), 2.27–2.43 (1H, m, 4'-CH), 2.86–3.06 (1H, m, 1-CH), 3.43–3.59 (1H, m), 3.60–3.72 (1H, m), 3.64 (1H, d, J=5.7, 6-CH), 3.74–3.92 (2H, m), 4.20–4.47 (2H, m, 1-CH and 5-CH), 5.23 (2H, s), 5.23 (1H, d, J=13.8), 5.51 (1H, d, J=13.8), 7.51 (2H, d), 7.66 (2H, d), 8.23 (4H, d).

(h) Synthesis of (5R,6R)-6-(2-Hydroxy-2-Propyl)-2-[(3S)-Pyrrolidine-3-Ylthio]-1-Carba-2-Penem-Carboxylic Acid (Compound S9)

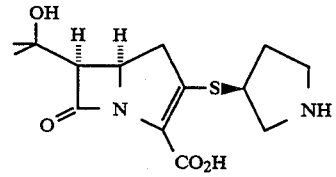

To a phosphate buffer (0.1M, pH 7.0)-THF solution (6:5, 5.5 ml) of Compound S8 (35.5 mg, 0.057 mmol) was added a 10% palladium carbon (18 mg), and the mixture was subjected to hydrogenolysis at normal pressure for 2.7 hours.

The palladium carbon was removed by filtration, the THF in the filtrate was removed by distillation under reduced pressure, and the residue was washed with ethyl acetate. The residual ethyl acetate was removed by distillation under reduced pressure. The residue was concentrated to about a 5 ml volume under reduced pressure and purified by an ion-exchange resin column chromatography ("Diaion HP-20", 15 φ×20 cm) at 4° C. Elution (about 0.5 ml/min) was carried out, using pure water, an aqueous 10% methanol solution and an aqueous 20% methanol in this order. The fractions of the desired compound were concentrated to about a 5 ml volume under reduced pressure and freeze-dried to obtain Compound S9 (pale yellowish-white solid, 8.8 mg, 50%).

Spectrum data of Compound S8;
IR (KBr): 3425, 1756, 1599, 1383 cm$^{-1}$.
NMR (D20, internal standard TSP-d$_4$): 1.31 (3H, s), 1.44 (3H, s), 2.05 (1H, m, 4'-CH), 2.49 (1H, m, 4'-CH), 3.07 (1H, dd, J=17.4, 10.2, 1-CH), 3.30–3.43 (2H, m, 2'-CH and 5'-CH), 3.51 (1H, m, 5'-CH), 3.66 (1H, dd, J=12.6, 6.6, 2'-CH), 3.75 (1H, d, J=5.7, 6-CH), 3.90 (1H, dd, J=17.4, 8.9, 1-CH), 4.05 (1H, m, 3'-CH), 4.33 (1H, ddd, J=10.2, 8.9, 5.7, 5-CH).

REFERENCE EXAMPLE 2

(a) Synthesis of Isopropyl (3S,5R,6S)-6-[(R)-1-Hydroxyethyl]-1-Carbapenam-3-Carboxylate (Compound S10)

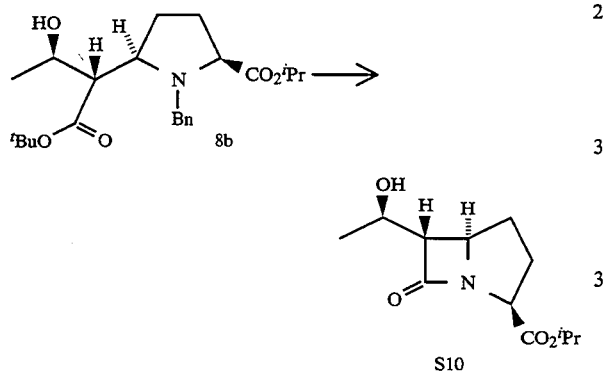

Acetic acid (0.85 ml, 14.9 mmol) was added to a methanol (55 ml) solution of a mixture of Compounds 8a, 8b and 8c (24:59: 17, 5.69 g, 14.0 mmol), and the mixture was subjected to hydrogenolysis using a 10% palladium carbon (250 mg) as the catalyst at normal pressure for 3.8 hours. The catalyst was removed by filtration, and the solvent was removed by distillaton under reduced pressure. The residue was dissolved in ethyl acetate, the solution was washed with an aqueous 5% sodium hydrogen carbonate solution. The aqueous layer was reverse-extracted with ethyl acetate. The ethyl acetate solutions were combined, washed with an aqueous NaCl-saturated solution and dried. The solvent was removed by distillation under reduced pressure. An N-deprotected material was obtained as a pale yellowish viscous liquid (4.17 g, 94.2%).

Under a dry atmosphere, to a dichloromethane (10 ml) solution of this N-deprotected material was added 4N hydrochloride/dioxane (50 ml) under ice-cooling, and the mixture was stirred at room temperature for 21 hours. The solvent was removed by distillation under reduced pressure, hexane was added to the residue and removed by distillation under reduced pressure. Further, hexane-dichloromethane was added to the residue and removed by distillation under reduced pressure. The atmosphere was in pressure reduced with a vacuum pump to give a pale yellowish foamy solid.

Under a dry atmosphere, to a dichloromethane (90 ml) solution of this foamy material were added triethylamine (2.4 ml, 18 mmol) and water-soluble carbodiimide (1-ethyl-3-[3-(dimethylamino)propyl]carbodiimide hydrochloride, 3.3 g, 17 mmol) under ice-cooling, and the mixture was stirred at room temperature for 20 hours. The solvent was removed by distillation under reduced pressure, water was added and the mixture was extracted with ethyl acetate. The ethyl acetate solution was washed with an aqueous NaCl-saturated solution and dried, and the solvent was removed by distillation under reduced pressure.

The residue was divided into three portions, and each portion was purified by a medium pressure silica gel column chromatography (Lobar size B, ethyl acetate-hexane 7:5→2:1). There were obtained a carbapenam ((6R,8R)-isomer, pale yellowish viscous liquid, 319 mg, 9.4%) derived from Compound 8a, and a mixture (76:24, pale yellowish viscous liquid, 2.06 g (containing about 5% of impurities), yield 58%. Yield of Compound S10 from Compound 8b was 75%) of Compound S10 and a carbapenam ((6S,8S)-isomer) derived from Compound 8c.

Spectrum data of Compound S10;
NMR: 1.26 (3H, d, J=6.0), 1.30 (3H, d, J=6.3), 1.32 (3H, d, J=6.3, 9-CH$_3$), 1.78–1.93 (1H m, 1-CH), 2.07–2.17 (1H, m, 1-CH), 2.27–2.43 (2H, m, 2-CH$_2$), 3.02 (1H, dd, J=6.0, 2.4, 6-CH), 3.71 (1H, ddd, J=9.5, 5.6, 2.4, 5-CH), 3.86 (1H, dd, J=6.6, 3.2, 3-CH), 4.19 (1H, m, 8-CH), 5.07 (1H, sept, J=6.3).

(b) Synthesis of Isopropyl (5R,6S)-6-[(R)-1-Hydroxyethyl]-3-Phenylseleno-1-Carbapenam-3-Carboxylate (Compound S11)

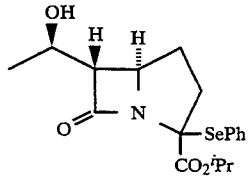

Under an argon atmosphere, n-butyl lithium (1.6M/hexane, 7.8 ml, 12.5 mmol) was added to a THF (35 ml) solution of diisopropylamine (1.92 ml, 13.7 mmol) at −70° C., and the mixture was stirred for 40 minutes. To the solution was added dropwise a THF (6 ml) solution of a mixture of Compound S10 and its (8S)-isomer (78:22, 1.20 g, 4.97 mmol, containing about 5% of impurities) at −70° C., and the mixture was stirred for 35 minutes. Subsequently, a THF (5 ml) solution of phenylselenyl chloride (1.43 g, 7.5 mmol) was added dropwise and the mixture was stirred for 8 minutes.

The reaction was stopped by adding an aqueous 20% ammonium chloride solution (18 ml). The reaction mixture was extracted with ethyl acetate, the ethyl acetate solution was washed with an aqueous NaCl-saturated solution and dried. The solvent was removed by distillation under reduced pressure. The residue was purified by a medium pressure silica gel column chromatography (Lobar size B, ethyl acetate-hexane 2:3→2:1) to obtain a mixture (78:22, yellowish viscous material, 1.04 g (containing about 5% of impurities), yield 50%) of a low polarity isomer of Compound S11 and its (8S)-isomer, and a mixture (72:28, 250 mg (containing about 5% of impurities), yield 11%) of a high polarity isomer of Compound S11 and its (8S)-isomer.

Spectrum data of Compound S11;

NMR of low polarity isomer: 1.27 (3H, d, J=6.3, 9-CH₃), 1.28 (6H, d, J=6.3), 1.29 (3H, d, J=6.3), 1.63 (1H, r-d, J=5, OH), 1 73-1.88 (1H, m, 1-CH), 1.94 -2.07 (1H, m, 1-CH), 2.40 (1H, ddd, J=14.1, 9.8, 6.8, 2-CH), 2.69 (1H, ddd, J=14.1, 7.7, 3.5, 2-CH), 2.90 (1H, dd, J=6.2, 2.2, 6-CH), 3.32 (1H, ddd, J=8.1, 6.0, 2.2, 5-CH), 4.10 (1H, m, 8-CH), 5.08 (1H, sept, J=6.3), 7.25-7.45 (3H, m), 7.65-7.75 (2H, m).

NMR of high polarity isomer: 1.16 (6H, d, J=6.3), 1.34 (3H, d, J=6 3 9-CH₃), 1.60-1.70 (1H, m, 1-CH), 2.03-2.14 (1H, m, 1-CH), 2.49 (1H, ddd, J=14.3, 6.9, 2.3, 2-CH), 2.86 (1H, ddd, J=14.3, 11.7, 6.2, 2-CH), 2.96 (1H, dd, J=6.8, 2.3, 6-CH), 3.81 (1H, ddd, J=9.0, 5.9, 2.3, 5-CH), 4.21 (1H, m, 8-CH), 4.85 (1H, sept, J=6.3), 7.25-7.45 (3H, m), 7.7-7.8 (2H, m).

(c) Synthesis of Isopropyl (5R,6S)-6-[(R)-1-Hydroxyethyl]-1-Carba-2-Penem-3-Carboxylate (Compound S12)

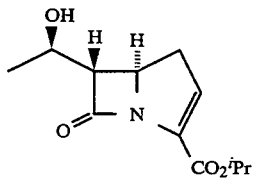

Under an argon atmosphere, to a dichloromethane (25 ml) solution of the mixture of Compound S11 and the (8S)-isomer thereof obtained in the preceding item (b) was added dropwise a dichloromethane (13 ml) solution of meta-chloroperbenzoic acid (1.23 g, 6.8 mmol) at −30° C. and the mixture was stirred for 35 minutes. Subsequently, at the same temperature, triethylamine (1.35 ml, 9.7 mmol) was added dropwise and the mixture was stirred for 32 minutes.

The reaction mixture was diluted with ethyl acetate, and washed with water. The aqueous layer was reverse-extracted with ethyl acetate. The ethyl acetate solutions were combined, washed with an aqueous NaCl-saturated solution and dried, and the solvent was removed by distillation under reduced pressure. The residue was purified by a medium pressure silica gel column chromatography (Lobar size B, ethyl acetate-hexane 1:1→3:2) to obtain a mixture (78:22, yellowish viscous material, 397 mg (containing about 5% of impurities), yield 51%) of Compound S12 and the (8S)-isomer thereof.

Spectrum data of Compound S12;

NMR: 1.308 (3H, d, J=6.3), 1.311 (3H, d, J=6.3), 1.35 (3H, d, J=6.3, 9-CH₃), 1.79 (1H, br-d, J=5, OH), 2.79 (1H, ddd, J=19.1, 8.3, 2.7, 1-CH), 2.95 (1H, ddd, J=19.1, 10.0, 3.0, 1-CH), 3.19 (1H, dd, J=6.8, 3.2, 6-CH), 4.25 (1H, m, 8-CH), 4.27 (1H, ddd, J=10.0, 8.3, 3.2, 5-CH), 5.15 (1H, sept, J=6.3), 6.42 (1H, dd, J=3.0, 2.7, 2-CH). Small coupling (<1 Hz) was observed between 2-CH and 6-CH.

(d) Synthesis of Isopropyl (5R,6S)-6-[(R)-1-Hydroxyethyl]-2-Ethylthio-1-Carbapenam-3-Carboxylate (Compound S13)

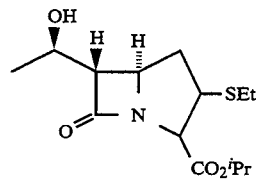

Under a dry atmosphere, to a dichloromethane (10 ml) solution of a mixture (86:14, 250 mg (containing about 8 of impurities)) of Compound S12 and a (8S)-isomer thereof were added ethanethiol (0.12 ml, 1.6 mmol) and DBU (0.045 ml, 0.30 mmol) at −30° C., and the mixture was stirred at the same temperature for 80 minutes.

The reaction mixture was diluted with ethyl acetate, washed with an aqueous 5% citric acid solution, an aqueous 5% sodium hydrogen carbonate solution and an aqueous NaCl-saturated solution, and dried. The solvent was removed by distillation under reduced pressure to obtain a crude product of a mixture of two isomers of Compound S13 (about 6:4, pale yellowish brown viscous material, 300 mg, crude yield 95%, purity was about 70%).

(e) Synthesis of p-Nitrobenzyl (5R,6S)-6-[(R)-1-Hydroxyethyl]-2-Ethylthio-1-Carbapenam-3-Carboxylate (Compound S14)

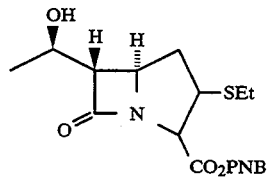

To a THF-water (2:1, 12 ml) solution of Compound S13 obtained in the above item (d) was added under ice-cooling an aqueous 1N sodium hydroxide solution (0.800 ml, 0.800 mmol) in 4 portions at every 20 minutes. The mixture was stirred under ice-cooling for 30 minutes and at room temperature for 3 hours. The THF was removed by distillation under reduced pressure and the residual aqueous solution was washed with ether (from the ether solution, Compound S13 (131 mg, 44%) was recovered). water was removed by distillation under reduced pressure to dryness. Under a dry atmosphere, para-nitrobenzyl bromide (184 mg, 0.85 mmol) was added to a DMF (5 ml) solution of the residue (yellowish candy-like material), and the mixture was stirred at room temperature for 5 hours.

In the same manner, the S13 recovered from the ether solution was subjected to hydrolysis and para-nitrobenzyl-esterification.

Both DMF solutions were combined and the DMF was removed by distillation under reduced pressure. The residue was diluted with ethyl acetate and washed with an aqueous NaCl-semisaturated solution. The aqueous layer was reverse-extracted with ethyl acetate, the ethyl acetate solutions were combined, washed with an aqueous NaCl-saturated solution and dried, and the solvent was removed by distillation under reduced pressure. The residue was purified by a medium pressure silica gel column chromatography (Lobar size B, ethyl acetate-hexane 1:1→2:1) to obtain an isomer of Compound S14 (colorless viscous material, 72 mg, 18%) and a mixture (72:28, pale yellowish viscous material, 29 mg, 7.4%) of S14 and the (8S)-isomer thereof.

Spectrum data of Compound S14;
IR (neat): 3453, 1749 cm$^{-1}$.
NMR: 1.24 (3H, t, J=7.5), 1.34 (3H, d, J=6.3), 1.66 (1H, br-d, J=5, OH), 1.73 (1H, ddd, J=13.7, 7.7, 6.9, 1-CH), 2.52–2.70 (3H, m, 1-CH and SCH$_2$), 3.11 (1H, dd, J=6.8, 2.4, 6-CH), 3.80 (1H, m, 2-CH), 3.92 (1H, td, J=6.8, 2.4, 5-CH), 4.21 (1H, br, 8-CH), 4.43 (1H, d, J=5.5, 3-CH), 5.28 (2H, s, PNB), 7.54 (2H, d), 8.24 (2H, d).

(f) Synthesis of p-Nitrobenzyl (5R,6S)-6-[(R)-1-Hydroxyethyl]-2-Chloro-2-Ethanesulfinyl-1-Carbapenam-3-Carboxylate (Compound S15)

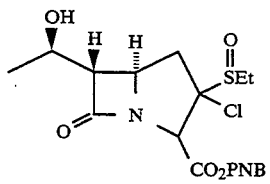

S15

Under a dry atmosphere, to a dichloromethane (4 ml) solution of Compound S14 (59 mg, 0.15 mmol) were added water (0.014 ml, 0.78 mmol) and pyridine (0.036 ml, 0.45 mmol), and further added dropwise a dichloromethane (2 ml) solution of iodobenzene dichloride (103 mg, 0.37 mmol) under ice-cooling, and the mixture was stirred at the same temperature for 30 minutes. Subsequently, triethylamine (0.042 ml, 0.30 mmol) was added and the mixture was stirred for 10 minutes.

The reaction mixture was diluted with ethyl acetate, washed with an aqueous 5% citric acid solution and water. The aqueous layer was reverse-extracted with ethyl acetate. The ethyl acetate solutions were combined, washed with an aqueous NaCl-saturated solution and dried. The solvent was removed by distillation under reduced pressure. The residue was purified by a medium pressure silica gel column chromatography (Lobar size A, ethyl acetate-hexane 3:2→1:0) to obtain a mixture (pale yellowish viscous material, 51 mg, 77%) of some isomers of Compound S15.

(g) Synthesis of p-Nitrobenzyl (5R,6S)-6-[(R)-1-Hydroxyethyl]-2-[(3S)-1-(p-Nitrobenzyloxycarbonyl)Pyrrolidine-3-Ylthio]-1-Carba-2-Penem-3-Carboxylate (Compound S16)

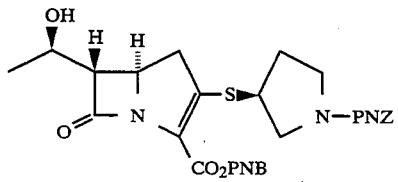

S16

Under an argon atmosphere, DBU (0.019 ml, 0.13 mmol) was added to a DMF (3 ml) solution of Compound S15 (51 mg, 0.11 mmol) at −30° C., and the mixture was stirred for 40 minutes. Subsequently, at the same temperature, a DMF (0.2 ml) solution of (S)-3-mercapto-1-(p-nitrobenyloxycarbonyl)pyrrolidine (41 mg, 0.15 mmol) was added and the mixture was stirred for 40 minutes.

An aqueous 5% citric acid solution was added and the mixture was extracted with ethyl acetate. The ethyl acetate solution was washed with an aqueous NaCl-saturated solution and dried, and the solvent was removed by distillation under reduced pressure. The residue was purified by a medium pressure silica gel column chromatography (Lobar size A, ethyl acetate-hexane 2:1→1:0) to obtain Compound S16. Yellowish viscous material, 44 mg. The material contained DMF (about 0.8 mg) and ethyl acetate (about 4.2 mg) and it is 39 mg (55.5%) as Compound S16.

Spectrum data of Compound S16;
IR (KBr): 3429, 1777, 1705 cm$^{-1}$.
NMR: 1.37 (3H, d, J=6.3), 1.9–2.1 (1H, m, 4'-CH), 2.25–2.45 (1H, m, 4'-CH), 3.10–3.34 (2H, m, 1-CH$_2$), 2.21 (1H, dd, J=6.9, 2.7, 6-CH), 3.40–3.59 (2H, m), 3.60–3.78 (2H, m), 3.87 (1H, dd, J=11, 6.5), 4.18–4.33 (2H, m, 5-CH and 8-CH), 5.23 (2H, s), 5.23 (1H, d, J=13.8), 5.51 (1H, d, J=13.8), 7.51 (2H, d), 7.65 (2H, d), 8.22 (4H, m).

INDUSTRIAL APPLICABILITY

As clearly seen from the above, according to the present invention, 6-hydroxy-6-hydroxyethylcarbapenams which are intermediates for the synthesis of 6-hydroxy-6-hydroxyethylcarbapenem derivatives useful as medicines can be produced more easily than by conventional methods. Also, the optically active pyrrolidine derivatives and a process for producing the same of the present invention are useful for the synthesis of carbapenems having a hydroxyalkyl group at the 6-position.

We claim:
1. Optically active pyrrolidine derivatives represented by the following formula (XI):

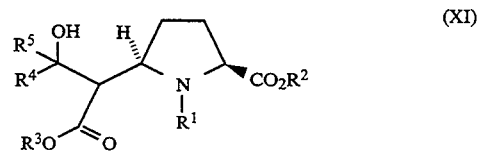

(XI)

wherein R$^1$ represents a benzyl group, R$^2$ represents an alkyl group having 1 to 6 carbon atoms, R$^3$ represents an alkyl group having 1 to 6 carbon atoms, a benzyl group or an allyl group, R$^4$ is selected from the group consisting of a hydrogen atom, an alkyl group having 1 to 6 carbon atoms which may be substituted with a protected hydroxyl group, a vinyl group, a phenyl group which may be substituted, a benzyl group which may be substituted, and a heterocyclic ring having 1 to 4 nitrogen or/and oxygen atoms, and R$^5$ represents a hydrogen atom or a methyl group.

2. An optically active pyrrolidine derivative according to claim 1 wherein R$^4$ is a hydrogen atom and R$^5$ is a methyl group.

3. An optically active pyrrolidine derivative according to claim 1 wherein R$^4$ and R$^5$ are both a methyl group.

* * * * *